United States Patent [19]

Gais et al.

[11] Patent Number: 4,964,846

[45] Date of Patent: Oct. 23, 1990

[54] PROCESS FOR THE E/Z STEREOSELECTIVE SYNTHESIS OF HOMOCHIRAL FIVE AND SIX RING INTERMEDIATE PRODUCTS

[75] Inventors: Hans-Joachim Gais; Irene Erdelmeier; Rolf Birk, all of Freiburg, Fed. Rep. of Germany

[73] Assignee: Schering Aktiengesellschaft, Berlin and Bergkamen, Fed. Rep. of Germany

[21] Appl. No.: 273,539

[22] Filed: Nov. 21, 1988

Related U.S. Application Data

[63] Continuation-in-part of Ser. No. 291,077, Nov. 16, 1988, abandoned.

[30] Foreign Application Priority Data

May 16, 1986 [DE] Fed. Rep. of Germany ....... 3616850

[51] Int. Cl.$^5$ .................. C07D 317/72; C07D 319/08; C07C 145/02

[52] U.S. Cl. ...................................... 549/336; 568/36; 564/102; 562/430; 556/422; 549/75; 549/491; 548/561; 548/341; 548/214; 548/146; 546/329

[58] Field of Search .................. 568/36; 564/102, 440; 549/333, 336, 341, 75, 491, 950; 562/430; 556/422; 548/561, 341, 146, 214; 546/329; 544/366, 335

[56] References Cited

PUBLICATIONS

Johnson et al., J. Org. Chem., 45, 264 (1980).
Johnson et al., JACS., 104, 4021 (1982).
Erdelmeier et al., Tet. Lett., 26, 4359 (1985).

Primary Examiner—Nicky Chan
Attorney, Agent, or Firm—Millen, White & Zelano

[57] ABSTRACT

This invention comprises a process for the production of unsymmetrical olefins from prochiral symmetrical ketones by addition of lithiosulfoximine from n-butyllithium and N-substituted S-methyl-S-phenyl-sulfoximine derivatives and then reaction with n-butyllithium/trimethychlorosilane.

19 Claims, No Drawings

PROCESS FOR THE E/Z STEREOSELECTIVE SYNTHESIS OF HOMOCHIRAL FIVE AND SIX RING INTERMEDIATE PRODUCTS

This application is a continuation-in-part of Ser. No. 07/291,077, filed on Nov. 16, 1988, now abandoned, which is the national phase of PCT/DE87/00231, filed on May 18, 1987.

The invention relates to a new process for the E/Z stereoselective synthesis of homochiral 5 and 6 ring intermediate products of the formula I

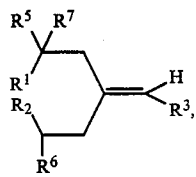

in which
$R^1$ and $R^2$ mean a common bond or the radical

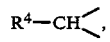

$R^3$ means the group

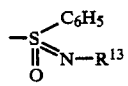

$R^4$ means a straight-chain or branched alkyl radical with 1-10 C atoms $R^5$ and $R^6$ are the same or different and mean hydrogen, alkyl with 1-10 C atoms, cycloalkyl with 5-7 C atoms, alkoxy with 1-6 C atoms, aryl with 6-10 C atoms, aralkyl win 7-12 C atoms or a 5-7-membered heterocycle, which can contain another N, O or S atom, or if $R^1$ and $R^2$ represent a common bond $R^5$ and $R^6$ jointly mean the radicals

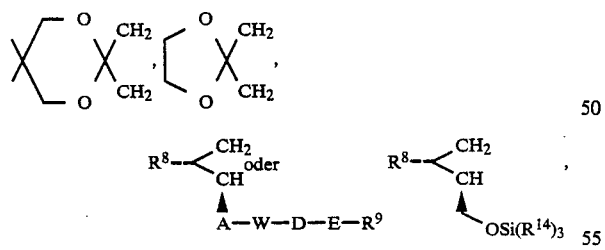

$R^8$ represents hydrogen, alkyl with 1-10 C atoms or $OR^{10}$ with $R^{10}$ meaning a hydrogen, a silyl radical or an ether radical or acid radical, A means a trans-CH=CH group or trans -C≡C group, W means a hydroxymethylene or -C(CH$_3$)(OH) group D means an alkylene group with 1-5 C atoms, E means a -C≡C- or —CH=CR$^{11}$ group, $R^9$ means an alkyl group with 1-6 C atoms, DER$^9$ means cycloalkyl with 5-6 C atoms or the radical

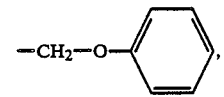

$R^{11}$ means alkyl with 1-4 C atoms, $R^7$ means the radicals —(CH$_2$)$_m$—R$^{12}$ or —(CH$_2$)$_m$-o—[Z$_1$—(CH$_2$)$_{m-p}$]$_x$—[Z$_2$—(CH$_2$)$_{m-q}$]$_y$—R$^{12}$, hydrogen, $R^{13}$ means alkyl with 1-4 C atoms or a tosyl radical, $R^{14}$ means alkyl with 1-4 C atoms, phenyl or benzyl, m=2-20 o, p and q are positive intetgers, each independently less than or equal to 16, x, y=0, 1 or 2, $Z_1$ represents a cis-CH=CH group, a trans-CH=CH group or a C≡C group, $Z_2$ means oxygen, sulfur, an NH—, and N-methyl group or a - C≡C group, and $R^{12}$ means a free or protected amino, methylamino, hydroxy, carboxy, mercapto or halogen characterized in that to prochiral symmetrical ketones of formula II

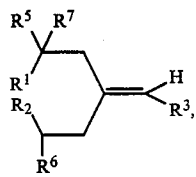

(all known or conventionally preparable) in which $R^1$, $R^2$, $R^5$, $R^6$ and $R^7$ have the meanings indicated above, is added lithiosulfoximine from n-butyllithium and an N-substituted S-methyl-S-phenyl-sulfoximine derivative of formula III

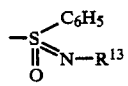

in which $R^{13}$ has the meaning already indicated, and then is reacted with n-butyllithium/trimethylchlorosilane.

The conversion of symmetrical ketones into unsymmetrical chiral olefins represents a largely unsolved problem. So far it has been possible to perform asymmetrical Wittig-like reactions only in particular cases by using reagents specially produced for this purpose [see S. Hanessian et al. JACS 106 (1984), 5754].

It has now been surprisingly found that especially lithiosulfoximines from n-butyllithium and chiral N-substituted S-methyl-S-phenylsulfoximine derivatives easily producible according to C. R. Johnson et al. [JACS 95 (1973), 7418] undergo addition to prochiral symmetrical ketones. Then reaction with an alkyllithium or aryllithium compound, preferably n-butyllithium/trimethylchlorosilane, leads to the unsymmetrical olefins of formula I which otherwise can be produced only with difficulty.

For the alkyl radicals $R^4$, $R^5$, $R^6$ and $R^8$ all straight-chain and branched radicals with 1-10 C atoms are suitable, such as, for example, methyl, ethyl, propyl, isopropyl, butyl, sec-butyl, tert-butyl, isobutyl, pentyl, isopentyl, neopentyl, hexyl, isohexyl, heptyl, octyl, nonyl, decyl. Preferred radicals are those with 1–6 C atoms.

As cycloalkyl with 5–6 C atoms for DER$^9$, R$^5$ and R$^6$, cyclopentyl and cyclohexyl and the respective methyl-substituted derivatives are meant.

The $C_{1-6}$ alkyl groups R$^9$, the $C_{1-4}$ alkyl groups R$^{11}$, R$^{13}$ and R$^{14}$ as well as the $C_{1-6}$ alkoxy groups R$^5$ and R$^6$ also correspond to the straight-chain and branched alkyl radicals already mentioned for R$^4$.

The aryl radicals with 6–10 C atoms (R$^5$ and R$^6$) in the first place are to represent phenyl, alpha- and beta-naphthyl.

The aralkyl radicals R$_5$ and R$_6$ with 7–12 C atoms are benzyl, phenethyl, 2-phenethyl, 3-phenylpropyl, alpha-naphthylmethyl, etc.

The most important 5–7-membered heterocycles, which can also contain another N, O or S atom, are pyrryl, furyl, thienyl, pyrazolyl, imidazolyl, thiazolyl, pyridyl, pyrimidinyl, pyrazinyl, azepinyl, diazephinyl, etc.

The hydroxy groups in W can be functionally modified, for example, by etherification or esterification, and the free or modified hydroxy groups in W can be in alpha or beta position, and the free hydroxy groups are preferred.

As ether radicals and acyl radicals (e.g., also for R$^{10}$) which are known to one skilled in the art are suitable. Easily cleavable ether radicals are preferred such as, for example, the tetrahydropyranyl, tetrahydrofuranyl, alpha-ethoxyethyl, trimethylsilyl, dimethyl tert-butylsilyl, tribenzylsilyl and diphenyl tert-butylsilyl radical. Acetyl, propionyl, butyryl, benzyl are suitable as acyl radicals.

Straight-chain or branched-chain, saturated alkylene radicals with up to 5 C atoms are suitable as alkylene group D, which optionally can be substituted by fluorine atoms, 1,2-methylene, 1,1-trimethylene, 1,1-tetramethylene or 1,1-pentamethylene. There can be mentioned, for example: methylene, fluoromethylene, ethylene, methylethylene, ethylethylene, trimethylene, tetramethylene, pentamethylene, 1-methyltetramethylene, 1-methyltrimethylene, pentametylene, 1-methyltetramethylene, 1-methyltrimethylene, 1,1-trimethylene ethylene, 1,1-tetramethylene ethylene.

For R$^7$ as —(CH$_2$)$_m$—R$^{12}$ alkylene groups with 2–20 C atoms are suitable which can also contain one or more groups Z$_1$ or Z$_2$, such as —(CH$_2$)$_{m-o}$—[Z$_1$—(CH$_2$)$_{m-p}$]$_x$—[Z$_2$—(CH$_2$)$_{m-q}$]$_y$—R$^{12}$ and m=2–20 and o, p and q together are less than or equal to 16, such as, for example, —(CH$_2$)$_5$—NH$_2$, —(CH$_2$)$_6$—NHCH$_3$, —(CH$_2$)$_2$—O—(CH$_2$)$_2$—COOH, —(CH$_2$)$_2$—O—(CH$_2$)$_3$—NH$_2$, —(CH$_2$)$_2$—O—(CH$_2$)$_2$—O—(CH$_2$)$_2$—OH,

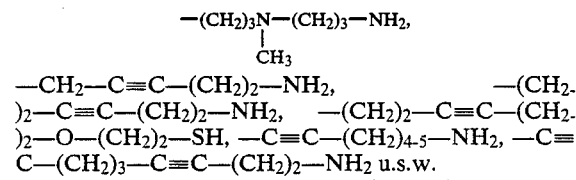

—CH$_2$—C≡C—(CH$_2$)$_2$—NH$_2$, —(CH$_2$)$_2$—C≡C—(CH$_2$)$_2$—NH$_2$, —(CH$_2$)$_2$—C≡C—(CH$_2$)$_2$—O—(CH$_2$)$_2$—SH, —C≡C—(CH$_2$)$_{4-5}$—NH$_2$, —C≡C—(CH$_2$)$_3$—C≡C—(CH$_2$)$_2$—NH$_2$ u.s.w.

According to the process according to the invention, the homochiral olefins of formula I can be prepared in high yields, and they precipitate practically in optically pure form. Thus, the new process proves far superior to the method described in Tetr. Letters 26, 4359 (1985) especially in the case of enolizable 5-ring ketones. Olefins with a bicyclo[3.3.0] octane ring skeleton represent especially interesting intermediate products, since they lead to biologically active (E) carbacyclines, such as, for example, Iloprost.

To attain these biologically interesting compounds, the sulfoximino group R$^3$ must be substituted in the olefins of formula I by a substituted alkyl radical, especially by a C$_4$ unit [cf., in this connection E. J. Corey et al., Tetr. Letters 24, 5571 (1983)] with the help of metal-organic methods such as, for example, that of M. Julia et al., Tetr. Letters 23, 2469 (1982).

The invention relates to the addition of chiral (R) or (S) phenylsulfoximine methylene lithium compounds to prochiral ketones of formula II, preferably cyclopentanone or cyclohexanone compounds, and then the reaction with an activated trialkyl silicon compound with cleavage of silanol lithium salts to chiral olefins of formula I corresponding to claim.

By protected amino groups R$^{12}$ is to be understood: acyl such as, e.g., acetyl, propionyl or benzoyl, urethane protecting groups such as, e.g., benzyloxycarbonyl, tert-butyloxycarbonyl or 9-fluorenylmethyloxycarbonyl and phthalimidoyl. This is to represent only a selection of possible protecting groups. By halogen as R$^{12}$ is meant fluorine, chlorine and bromine.

Instead of n-butyllithium in the combination n-butyllithium/trimethylchlorosilane, still other arlkyl or aryl lithium derivatives are suitable such as, e.g., CH$_3$Li, C$_2$H$_5$Li, C$_3$H$_7$Li, tert-butyl Li, sec-butyl Li or phenyl Li.

The reaction conditions in the examples represent only preferred conditions.

This invention, of course, also includes all modifications that can be made by one wtih average skill in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications cited above and below, and of corresponding PCT application PCT/DE87/00231 are hereby incorporated by reference.

EXAMPLES

Procedure A 1 for the production of 2-hydroxysulfoximines 2, 5, 10 and 12

1 equivalent of a 1.5 normal solution of n-butyllithium in n-hexane is instilled in a solution of N,S-dimethyl-S-phenylsulfoximine (1) in absolute THF under nitrogen at 0° C. so that the temperature of the solution does not rise above 5° C. After addition is completed, stirring is performed for 15 more minutes at 0° C. and then the light yellowish solution of the lithiumsulfoximine is cooled to −78° C. An equivalent of the corresponding carbonyl compound, dissolved in a few ml of absolute THF, is added once with a syringe, as a result of which the temperature of the solution rises by 5–20 degrees. After the exothermic reaction has quieted down, the cooling agent is removed and warming to room temperature is allowed. 1 hour after addition of the carbonyl compound the reaction mixture is quenched with saturated NH4Cl solution and extracted with ethyl acetate, and in general one extraction is sufficient (TLC checking; very sensitive coloring reaction with anisaldehyde-glacial acetic acid spray reagent). After drying with MgSO4, concentration by evaportion in a vacuum and LC on silica gel (hexane/ethyl acetate mixture) the products are obtained as colorless crystalline solids. Since the Rf value of the adducts is between initial compound 1 and the respective carbonyl compound, with LC unreacted carbonyl compound can be recovered at the same time.

Procedure A 2 for the production of 1-alkenylsulfoximines 3, 6, 8 11 and 13

Exactly one equivalent of a 1.5 normal solution of n-butyllithium in n-hexane is added to one equivalent of the addition product according to A 1 in absolute THF under $N_2$ at 0° C., and with the addition of the last drop the reaction solution suddenly takes on a yellow color. It is stirred for 15 minutes at 0° C., then cooled to −78° C., 1.3 equivalents of trimethylchorosilane (pure or as a solution in absolute hexane) is added all at once and allowed to warm to room temperature. After 3 h at room temperature, the solution, which is again colorless in the meantime, is cooled to −78° C. and 1 equivalent of the n-butyllithium solution instilled (with orange coloring of the solution) and is stirred at −70° C. to −90° C. After completion of the reaction after 0.5-2.5 h (TLC: the products basically have a smaller Rf value than the feedstock) it is quenched with a saturated NH4Cl solution and extracted with ethyl acetate. After drying with MgSO4 and concentration by evaporation the product is obtained after LC on silica gel with hexane/ethyl acetate mixtures; incompletely reacted feedstock can be recovered by LC.

(1.)
(±)-1-[N-methyl-S-phenylsulfonimidoyl]-cyclopentanol (2)

According to A 1, 3.38 g (20 mmol) of (±)-N, S-dimethyl-S-phenyl-sulfoximine 1 in 50 ml of absolute THF is metalated with 13.3 ml (20 mmol) of a butyllithium-n-hexane solution and then reacted with 1.68 g (20 mmol) of cyclopentanone. After LC on 130 g of silica gel (n-hexane/ethyl acetate 1:1), 4.7 (93%) of (±)-2 is obtained at colorless crystalline compound. Melting point: 67°-68° C. (hexane/ethyl acetate)

$C_{13}H_{19}NO_2S$ (253.4) cal. C 61.63, H 7.56, N 5.53; fnd. C 61.34, H 7.65, N 5.48.

$^1$H-NMR (300 MHz, CDCl3): δ=1.33-2-23 (m, 8H, 2-H, 4-H, 5-H), 2.61 (s, 3H, N-CH3), 3.10 (d, 1H, J=14 Hz, 6-H), 3.57 (d, 1H, J=14 Hz, 6-H), 6.24 (s, breit, 1H, —OH), 7.52-7.67 (m, 3H, Ar-H), 7.83-7.91 (m, 2H, Ar-H).

MS (EI, 70 eV): m/z (%)=253 (M+,4), 211 (18), 156 (80), 140 (59), 125 (PhSo, 100), 107 (66), 106 (32), 91 (28), 81 (40), 78 (48), 77 (40), 51 (28), 41 (32).

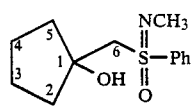

(2.)
(±)-S-cyclopentylidenemethyl-N-methyl-S-phenylsulfoximine (3)

760 mg (3 mmol) of (±)-2 in 30 ml of absolute THF is reacted according to A 2, and the elimination is already complete in 15 minutes after addition of the second equivalent of n-butyllithium. After column filtration over silica gel (hexane/ethyl acetate 1:1), 700 mg (99%) of colorless crystalline (±)-3 is obtained, melting point: 81°-82° C. (ethyl acetate).

$C_{13}H_{17}NOS$ (235.3) cal. C 66.35, H 7.28, N 5.95; fnd. C 66.22, H 7.22, N 6.09.

$^1$H-NMR (300 MHz, CDCl3): δ=1.52-1.80 (m, 4H, 3-H, 4-H), 2.26-2.50 (m, 3H, 2-H, 5-H), 2.67 (s, 3H, N-CH3), 2.78-2.94 (m, 1H, 2-H), 6.31 (quint, 1H, J=2.5 Hz, 6-H), 7.48-7.62 (m, 3H, Ar-H), 7.86-7.94 (m, 2H, Ar-H).

MS (EI, 70 eV): m/z (%)=236 (M++1, 15), 235 (M+, 77), 234 (M+-1, 16), 207 (12), 205 (19), 189 (15), 187 (42), 157 (36), 156 (50), 155 (100), 129 (51), 126 (12), 125 (22), 115 (17), 110 (15), 109 (33), 107 (13), 106 (14), 105 (12), 97 (14), 91 (30), 81 (49), 79 (75), 78 (30), 77 (63), 67 (30), 65 (18), 53 (40), 51 (44), 50 (12), 46 (12), 43 (61), 52 (65), 40 (41).

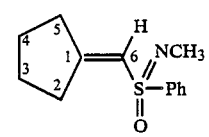

(3.)
(±)-5'-[[(N-methyl-S-phenyl-sulfonimidoyl)]-methyl]-tetrahydrospiro-[1,3-dioxolane-2,2'-(3'aalpha,5'beta,6-'aalpha)-1H,3'H-pentalen-5'ol [(±)5] and [(±)-5' (S)-5]

(a) (±)-5

1.69 g (10 mmol) of (±)-1 is metalated in 50 ml of absolute THF according to A 1 and reacted with 1.82 g (10 mmol) of [spiro-1',3'-dioxolane-2,2'-tetrahydro (1H)-pentalen]-5 (3H)-one (4) at −78° C. After 15 minutes at −78° C., the reaction is almost complete. LC of the raw product on 130 g of silica gel (hexane/ethyl acetate 1:2) yields 3.4 g (96%) of (±)-5 in colorless long needles, metlting point: 105°-108° C.

$C_{18}H_{25}NO_4S$ (351.5) cal. C 61.50, H 7.17, N 3.98: fnd. C 61.37, H 7.22, N 4.01.

(b) (±)-5'(S)-5

2.03 g (12 mmol) of S-1 (ee is greater than or equal to 96%) is reacted as in (a) with 2.18 (12 mmol) of 4. 3.88 g (92%) of (±)-[5'(S)]-5 is obtained in long needles, melting point 132°-133° C., [α]=+36.4° [α]$_{546}^{20}$=+43.5° (c=1.6 in acetone). By increasing the feedstock, 75% of the product can be obtained pure by a single recrystallization of the raw mixture (hexane/ethyl acetate), the rest is obtained by subsequent LC of the mother liquid concentrated by evaporation.

cal. 61.50, H 7.17, N 3.98; fnd C 61.50, H 7.22, N 3.98.

$^1$H-NMR (300 MHz, CDCl3): δ=1.70 (dd, 1H, $J_{1'a,1'\beta}$=13 Hz, $J_{a'\beta,6'aa}$=9 Hz, 1'Ha (oder 3'-Ha), 1.83 (dd, 1H, $J_{1'\beta,1'a}$=13 Hz, $J_{1'\beta,6'aa}$=6 Hz, 1'-Hβ (order 3'-Hβ), 1.88-2.10 (m, 5H, 2×1'-H) (order 2×3'-H), 2×6'-H, 4'Hβ), 2.42-2.55 (m, 2H, 3a'-Ha, 6a'-Ha), 2.63 (s, 3H,N-CH3), 2.60-2.74 (ddd, 1H, $J_{4'a,4'\beta}$=15 Hz, $J_{4'a/3'aa}$=8 Hz, $J_{4'a/6'a}$=2 Hz, 4'-Ha), 3.06 (d, 1H, J=14

Hz, 7'-H), 3.46 (d, 1H, J=14 Hz, 7'-H), 3.90 (m, 4H, 4-H, 5-H), 6.43 (s, breit, 1H, —OH), 7.55–7.70 (m, 3H, Ar-H), 7.84–7.93 (m, 2H, Ar-H).

MS (EI, 70 eV): m/z (%)=351 (M+,13), 196 (17), 182(μl), 169(14), 156 (100), 154 (PhSONCH₃, 37), 140 (36), 139 (PhSON, 24), 135 (14), 125 (PhSO, 85), 113 (38), 112(32), 107 (40), 106(30), 99(21), 95(27), 91 (19), 86 (24), 79(11), 78(19), 77(39), 55(13), 51 (20), 43(25), 41(48), 39(17).

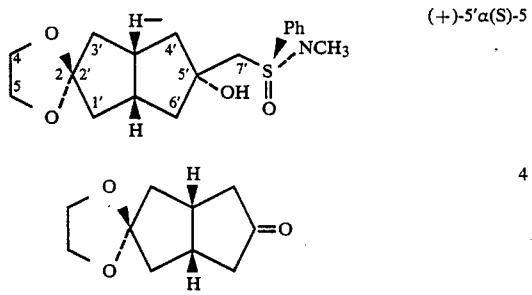

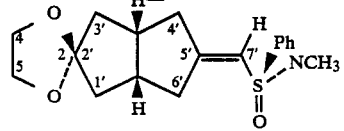

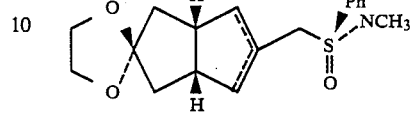

(4.)
(±)-S-spiro-[1,3-dioxolane-2,2'-[(3'aalpha,6'aalpha)tetrahydro(1H,3H)-5-pentalenoylidene]]methyl-N-methyl-S-phenylsulfoxamine[(−)-[(aR)-S-(S)]-6] and [(±)-6]

(a) (±)-6

525 mg (1.5 mmol) of (±)-5 in 30 ml of absolute THF is reacted according to A 2, is worked up 90 minutes after addition of the second equivalent of the n-butyllithium solution. LC on 100 g of silica gel (ethyl acetate) yields 450 mg (90%) of a light yellowish oil, which consists of diastereomeric pure (±)-6 of (de greater than or equal to 96%, according to ¹H-NMR at 300 MHz), besides 11% of isomerized (±)-6i.

(b) (−)-[(aR)-S(S)]-6

525 mg (1.5 mmol) of (±)-[5' (S)]-5 is reacted as in (a). The product (−)-[(aR)-S-(S)]-6,[α]$_D^{20}$=64.9° (c=1.5 in CH₂Cl₂) contains 14% of isomerized compound 6i.

C₁₈H₂₃NO₃S (333.1) cal. C 64.83, H 6.95, N 4.20; fnd. C 64.43, H 6.96, N 4.06. (333.1412 333.14134 high resolution)

¹H-NMR (300 MHz, CDCl₃) mixture of 6 and 6i 6:=1.56–1.70 (2×dd, 2H, J₁'α/1'β=J₃'α/3'β=15 Hz, J₃'/3'a=J₁'/6'aa=8 Hz, 1-H,3-H), 1.96–2.10 (2×dd, J=15 Hz, J=8 Hz, 1-H, 3-H), 2.23–3.17 (m, 6H, 4-H, 6-H, 3a-Ha, 6a-Ha), 2.68 (s, 3H, N-CH₃), 3.86 (s, 4H, 4-H, 5-H), 6.27 (quint, 1H, J=2 Hz, 7'-H), 7.48–6.63 (m, 3H, Ar-H), 7.80–7.94 (m, 2H, Ar-H).

For 6i only the protons with different chemical shifts in comparison with 6 are indicated.

6i: δ=1.23–1.38 (m, 1'-H/3'-H), 1.43–1.56 (m, 1'-H/3'-H), 1.85–1.96 (m, 1'-H/3'-H), 2.71 (s, N-CH₃), 2.72 (s, N-CH₃), 3.87 (s, 4-H, 5-H), 3.95 (s, breit, 7-H), 5.21 (m, 4-H), 5.27 (m, 4-H).

¹³C-NMR (75.47 MHz, CDCl₃): 6: δ=29.22 (q, N-CH₃), 35.86 (t), 39.20, 41.19 (2×d, 3'a-C, 6'a-C), 41.66, 41.69, 42.05 (3x t, 1'-C, 3'-C, 4'-C, 6'-C), 63.94, 64.53 (2×t, 4-C, 5-C), 118.46 (s, 2-C), 122.42 (d, 7'-C), 128.53, 129.01 (2×d, Ar-C), 132.12 (d, Ar-C), 140.97 (s, Ar-C), 163.72 (s, 7'-C).

6i: δ=30.0, 38.67, 39.84, 41.54, 41.89, 42.17, 47.51, 58.35, 64.71, 117, 129.62, 129.69, 132.73, 138.49.

MS (EI, 70 eV): m/z (%)=333 (M+, 100), 246(55), 208 (M+-PhSO,32), 179 (M+-PhSONCH₃, 38).

(5.)
(±)-cis/trans-4-(1,1-dimethylethyl)-1-[(N-methyl-S-phenylsulfonimidoyl)-methyl]-cyclohexanol
(±)-7a/(±)-7b and (±)-7a/(±)-7b (a) (±)-7b, (±)-7a According to C. R. Johnson, C. N. Schroeck and J. R. Shanklin, JACS 95, 7424 (1973) the addition of (±)-1 to t-butylcyclohexanone yields a crystalline mixture of (±)-7a and (±)-7b. By crystallization from n-hexane pure (±)-7a is obtained besides a mixture of (±)-7a:(±)-7a-5.4:1 enriched by (±)-7b (according to ¹H-NMR, 300 MHz).

(b) (±)-7a/(±)-7b

Analogously to (a), S-1 is reacted with t-butylcyclohexanone and the purified mixture (±)-7, which consists 29% of 7a and 71% of 7b (from ¹H-NMR, 300 MHz) is used without further crystallization in example 6c.

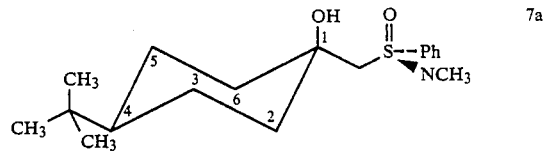

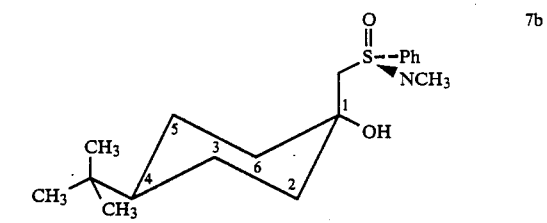

(6.)
(±)-S-[[4-(1,1-dimethylethyl)-cyclohexylidene]-methyl]-N-methyl-S-phenyl-sulfoximine (±)-8a, (±)-8b and (±)-(aS)-8a and (−)-(aR)-8b (a) Reaction of (±)-7a/(±)-7b 965 mg (3 mmol) of the mixture of (±)-7a and (±)-7b (1:5.4) produced according to 5(a) is reacted in 50 ml of absolute THF according to A 2. It is worked up 2 h after addition of 2 equivalents of n-butyllithium solution as described; after LC on 100 g of silica gel (ethyl acetate/hexane 2:1), 850 mg (93%) of a colorless oil, which solidifies in the refrigerator is obtained. According to ¹H-NMR (300 MHz) the product consists of the diastereomers (±)-8a and (±)-8b in a ratio of 87:13. The two diastereomers can be detected separately by thin-layer chromatography.

C₁₈H₂₇NOS (305.5) cal. C 70.77, H 8.91, N 4.58; fnd. C 70.81, H 8.91, N 4.58.

(b) reaction of (±)-7a 483 mg (1.5 mmol) of (±)-7a is reacted in 30 ml of absolute THF as in (a). LC of the raw mixture on 100 g of silica gel (hexane/ethyl acetate 1:1) yields, besides 110 mg (23%) of unreacted (±)-7a (from ¹H-NMR, 330 mg (72%, 94% relative to the reaction) of the diastereomers (±)-8a and (±)-8b in a ratio of 31:69 (from ¹H-NMR, 300 MHz).

Since obviously the selectivity of the elimination from 7a is the opposite of 7b, by the tests 6a and 6b the selectivity of elimination of pure 7b can also be calculated.

|  |  | (±)-8a:(±)-8b |
|---|---|---|
| Elimination of | (±)-7a: | 31:69 |
| Elimination of | (±)-7a/(±)7b (1:5:4): | 87:13 |
|  | 7b: | 98:2 |

(c) Reaction of (±)-7a/7b 970 mg (3 mmol) of (+)-7a/7b (29% of 7a, 71% of 7b) is reacted in 30 ml of absolute THF according to A 2. It is worked up 1 hour after addition of 2 equivalents of n-butyllithium; according to LC on 130 g of silica gel (ethyl acetate/hexane 1:1), 865 mg (95%) of the diastereomers (±)-(aS)-8a and (−)-(aR)-8b in a ratio of 78:22 (from ¹H-NMR, 300 MHz) are obtained. The two diastereomers can be isolated by LC on fine silica gel. (±)-(aS)-8a in colorless long needles with a melting point of 72° (hexane)[α]$_D^{20}$=+46°, [α]$_{546}^{20}$=+51° (c=0.5 acetone) and (−)-(aS)-8b as weakly yellowish oil: [α]$_D^{20}$=−99°, [α]$_{546}^{20}$=−123° (c=0.25 in acetone).

(±)-(aS)-8a

C₁₈H₂₇NOS (305.5) cal. C 70.77, H 8.91, N 4.58; fnd. C 70.66, H 8.97, N 4.50.

The configuration or the chiral axis in the molecule could be established as "S" by X-ray structure analysis of a monocrystal of (±)-(aS)-8a grown from hexane.

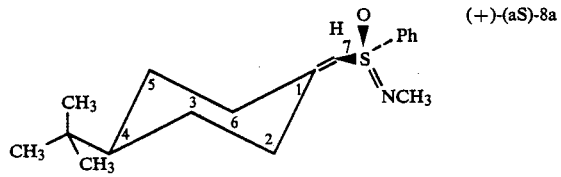

(+)-(aS)-8a

¹H-NMR (300 MHz, CDCl₃): δ=0.56 (dq, 1H, J$_{3a/2a}$=14 Hz, J$_{3a/3e}$=13 Hz, J$_{3a/4a}$=12.5 Hz, J$_{3a/2e}$=2.5 Hz, 3-Ha), 0.75 (s, 9H, tert-Butyl-H), 1.03 (dq, 1H, J$_{5a/4a}$=13 Hz, J$_{5a/6a}$=12.5 Hz, J$_{5a/5e}$=12 Hz, J$_{5a/6e}$=4 Hz, 5-Ha), 1.15 (tt, 1H, J$_{4a/5a}$=13 Hz, J$_{4a/3a}$=12.5 Hz, J$_{4a/5e}$=3 Hz, 4-Ha), 1.72 (dddd, 1H, J$_{3e/3a}$=13 Hz, J$_{3e/2a}$=5 Hz, J$_{3e/2e}$=2.5 Hz, 3-He), 1.84 (tdd, 1H, J$_{2a/2e}$=J$_{2a/3e}$=5 Hz, J$_{2a/7}$=1 Hz, 2-Ha), 1.90 (dddd, 1H, J$_{5e/5a}$=12 Hz, J$_{5e/6a}$=4 Hz, J$_{5e/6e}$=3,5 Hz, J$_{5e/4a}$=3 Hz, 5-He), 2.13 (dddd, 1H, J$_{6a/6e}$=13 Hz, J$_{6a/5a}$=12.5 Hz, J$_{6a/5e}$=4 Hz, J$_{6a/7}$=1 Hz, 6-Ha), 2.28 (dddd, 1H, J$_{6e/6a}$=13 Hz, J$_{6e/5a}$=4 Hz, J$_{6e/5e}$=3.5 Hz, J$_{6e/2e}$=2.5 Hz, 6-He), 2.66 (s, 3H,N-CH₃), 3.44 (dq, 1H, J$_{2e/3a}$=J$_{2e/3e}$=J$_{2e/6e}$=2.5 Hz, 2-He), 6.40 (s, breit, 1H, 7-H), 7.48–7.66 (m, 3H, Ar-H), 7.84–7.96 (m, 2H, Ar-H).

(−)-(aR)-8b

C₁₈H₂₇NOS (305.5) cal. C 70.77, H 8.91, N 4.58; fnd. C 70.43, H 9.17, N 4.40.

¹H-NMR (300 MHz, CDCl₃): δ=0.82 (s, 9H, tert-Butyl-H), 1.07-1.32, (m, 3H, 3-Ha, 3-He, 5-Ha), 1.56 (tdd, 1H, J$_{6a/6e}$=13 Hz, J$_{6a/5a}$=13 Hz, J$_{6a/5e}$=3 Hz, J$_{6a/7}$=1 Hz, 6-Ha), 1.82–1.98 (m, 2H, 4-Ha, 5-He), 2.07 (m, 1H, J$_{2a/2e}$=14 Hz, J$_{2a/3a}$=14 Hz, J$_{2a/7}$=1 Hz, J$_{2a/3e}$=? Hz, 2-Ha), 2.29(dddd, 1H, J$_{2e/2a}$=14 Hz, J$_{2e/3a}$=2.5 Hz, J$_{2e/6e}$=2 Hz, 2-He), 2.65 (s, 3H, N-CH₃), 3.54 (dq, 1H, J$_{6e/6a}$=13 Hz, J$_{6e/2e}$=J$_{6e/5a}$=J$_{6e/5e}$=2 Hz, 6-He),6.40 (s, 1H, breit, 7-H), 7.46–7.54 (m, 3H, Ar-H), 7.80–7.96 (m, 2H, Ar-H).

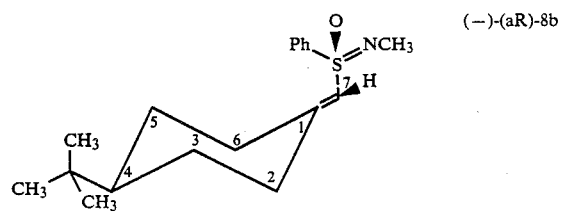

(−)-(aR)-8b

¹³C-NMR (75.47 MHz, CDCl₃): mixture of 8a and 8b
8a: δ=27.41 (q, CMe₃), 28.06, 28.67, 28.95 (3xt, 2- oder 6-C, 3-C), 29.12 (q, N-CH₃), 32.28 (s, CME₃), 37.26 (t, 2- oder 6-C), 47.25 (d, 4-C), 123.54 (d, 7-C), 128.59, 128.99 (2xd, Ar-C), 132.06 (d, Ar-C), 141.46 (s, Ar-C), 159.91 (s, 1-C).

For 8b only the C atoms are listed that have a chemical shift other than in 8a.

8b: δ=27.51 (3xq, CME₃), 29.31 (q, N-CH₃), 32.43 (s, CMe₃), 37.34 (t, 2-oder 6-C), 47.38 (d, 4-C), 123.44 (d, 7-C), 128.54, 128.99 (2xd, Ar-C).

MS (EI, 70 eV): m/z(%) 305 (M⁺, 6), 169 (14), 142 (21), 141 (24), 91 (22), 77 (25), 57 (C₄H₉, 100), 41 (80).

(7) [3aS-(2alphabeta,3-alphabeta, 4beta, 5alpha, 6abeta)]-5-[[(1,1-dimethyl)-dimethylsilyl]-oxy]-4-[[[1,1-dimethylethyl)-dimethylsilyl]-oxy]-methyl]2beta (R)-[[(N-methyl-S-phenyl)-sulfonimidoyl]-methyl]-hexahydro-pentalen]-2alpha(1H)ol (10)

152 mg (0.9 mmol) of S-1 (ee is greater than or equal to 95%) is reacted according to A 1 with 360 mg (0.9 mmol) of [3aS-(3aalpha,4alpha,5beta,6aalpha]-5-[[(1,1-dimethylethyl)-dimethylsily]-oxy]-4-[[[(1,1-dimethylethyl)-dimethylsily]-oxy]-methyl]-hexahydro-2 (1H)-pentalenone (9). LC on 100 g of silica gel (hexane/ethyl acetate 3:1) yields 480 mg (94%) of 10 as colorless oil, which thoroughly crystallizes after a few days in the refrigerator. The crystallization can also be accelerated by repeated concentration by evaporation with anhydrous hexane, melting point 65°–66° C. [α]$_D^{20}$=+13°, [α]$_{546}^{20}$=+24° (c=0.24 in acetone). The amount of rotation is very dependent on the temperature.

C₂₉H₅₃NO₄S Si₂ (567.99) cal. C 61.33, H 9.41, N 2.47; fnd. C 61.52, H 9.51, N 2.39.

¹H-NMR (300 MHz, CDCl₃): δ=0.03, 0.04, 0.05, 0.06 (4xs, 12H, SitBuMe₂), 0.88, 0.90 (2xs, 18H, SitBuMe₂), 1.67 (ddd, 1H, J$_{6a/6β}$=14 Hz, J$_{6a/5β}$=9 Hz, J$_{6a/6aβ}$=7-8 Hz, 6-Ha), 1.67 (dd, 1H, J$_{1β/1a}$=13,5 Hz, J$_{1β/6aβ}$=8 Hz, 1-oder 3-Hβ), 1.83 (dd, 1H, J$_{1a/1β}$=13.5 Hz, J$_{1a/6aβ}$=4 Hz, 1-oder 3-Ha), 1.96–2.1 (ddt, J$_{4a/8}$=7,5 Hz, J=4 Hz, 4-Ha und ddd, 1H, J$_{6β/6a}$=14 Hz, J=7 Hz, 6-Hβ), 2.15 (dd, 1H, j$_{3a}$=13 Hz, J$_{3a/3aβ}$=2 Hz, 3-oder 1-Ha), 2.2–2.40 (dd, 1H, J$_{3a/3\beta}$=13 Hz, 3-oder 1-H$\beta$ und m, 1H, 3a-H$\beta$ und m, 1H, 6a-H$\beta$), 2-62 (s, 3H, N-CH$_3$), 3.05, (d, 1H, J=14 Hz, 7-H), 3.49 (d, 1H, J=14 Hz, 7-H), 3,63 (2xdd, 2H, J=13 Hz, J$_{8/4a}$=4 Hz, 8-H), 3.90 (m, 1H, J=9 Hz, J=7.5 Hz, 5-H$\beta$), 6.35 (s, broad, 1H, —OH), 7.52–7.68 (m, 3H, Ar-H), 7.84–7.92 (m, 2H, Ar-H).

$^{13}$C-NMR (75.47 MHz, CDCl$_3$): δ=−5.4, −5.3, −4.7, −4.4 (4xq, SitBuMe$_2$), 18, 1. 18.4 (2xs, SitBuMe$_2$), 25.9, 26.1 (2xq, SitBuMe$_2$), 28.96 (q, N-CH$_3$), 37.2, 41.9 (2xd, 3a-C, 6a-C), 41.8, 44.0, 47.4 (3xd, 1-C, 3-C, 6-C), 56.2 (d, 4-C), 62.4, 64.4 (2xt, 7-C, 8-C), 74.8 )d, 5-C) 82.1 (s, 2-C), 129.1, 129.5 (2xd, Ar-C), 132.9 (d, Ar-C), 139.5 (s, Ar-C).

MS (EI, 70 eV): m/z (%)=567 (M$^+$, 3), 552 (M$^+$−15.3) 510 (M$^+$−C$_4$H$_9$, 72) 341 (48), 156 (51), 147 (100), 131 (23), 125 (PhSO, 35), 107 (20), 106 (21), 89 (28), 84 (32), 75 (33), 73 (95).

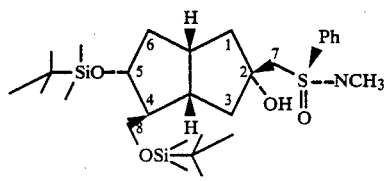

(8)

[3aS-(2Z,3aalpha,4alpha,5beta,6aalpha)]-S(R)-[5-[[(1,1-dimethylethyl)-dimethylsilyl]-oxy]-4-[[[(1,1-dimethylethyl)-dimethylsilyl]-oxy]-methyl]-hexahydro-2(1H)-pentalenoylidene]-methyl-N-methyl-S-phenyl-sulfoximine (11)

595 mg (1.05 mmol) of 10 is reacted according to A 2. It is worked up 2 hours after addition of the second equivalent of n-butyllithium solution. LC on 130 g of silica gel (hexane/ethyl acetate 1:1) yields, besides 70 mg (12%) of unreacted 10, 490 mg (85% relative to reaction 96%) of 11 as colorless oil, which crystallizes very slowly in the course of several days in the refrigerator, melting point 49°–51°, [α]$_D^{20}$=−79°, [α]$_{546}^{20}$=−96° (c=0.65 in acetone).

According to $^1$H-NMR (300 MHz) the diastereomer pure product still contains 3–10% of isomerized compound 11, and it still has not been settled whether the isomerization takes place by being basically catalyzed before working up or acidly catalyzed during or after working up.

C$_{29}$H$_{51}$NO$_3$SSi$_2$ (549.3) cal. 63.33, H 9.35, N 2.55; fnd. 63.43, H 9.62, N 2.52.

(549.3110, 549.31117 high resolution)

$^1$H-NMR (300 MHz, CDCl$_3$): δ=0.0, 0.01, 0.03 (2xs, 6H und 1xs, 6H, SitBuMe$_2$), 0.84, 0.88 (2xs, 18H, SitBuMe$_2$), 1.27 (ddd, 1H, J$_{6\beta/6a}$=13 Hz, J$_{6\beta/5a}$=7.5 Hz, J$_{6\beta/6aa}$=6 Hz, 6-H$\beta$), 1.53 (ddt, 1H, J$_{4\beta/5a}$=7.5 Hz, J$_{4\beta/3aa}$=7.5 Hz, J$_{4\beta/8}$=4 Hz, 4-H$\beta$), 2.04 (ddd, 1H, J$_{6a/6\beta}$=13 Hz, J$_{6a/5a}$=7,5 Hz, J$_{6a/6aa}$=7 Hz, 3-Ha), 2.34 (m, 2H, 3a-Ha, 6a-Ha), 2.39 (dd, 1H, J=17−18 Hz, 1-H$\beta$), 2.46 (dd, 1H, J$_{3a/3\beta}$=18 Hz, J$_{3a/3aa}$=7 Hz, 3-Ha), 2.61 (dd, 1H, J$_{1a/1\beta}$=17−18 Hz, J$_{1a/6aa}$=7.5 Hz, 1-Ha), 2.67 (s, 3H, N-CH$_3$), 2.95 (dd, 1H, J$_{3\beta/3a}$=18 Hz, J$_{3\beta/3aa}$=2 Hz, 3-H$\beta$), 3.56 (m, 2H, 8-H), 3.90 (q, 1H, J=7.5 Hz, 5-Ha), 6.24 (m, 1H, 7-H), 7.42–7.60 (m, 3H, Ar-H), 7.8–7.9 (m, 2H, Ar-H).

The allocation of the protons was successfully performed by uncoupling experiments. A clear determination of the Z stereochemistry of the double bond took place by $^1$H-NOE differential measurement, performed by H. Guenther, Siegen. Irradiation at 7-H lead to NOE for 1-Halpha, 1-Hbeta and thus proves that the deep field shift of 3-Hbeta, as expected, is caused by the anistropy effect of the sulfoximine function, in other words, 3-Hbeta and the grouping are placed in the cis-position. Irradiation in the case of 3-Hbeta leads to an NOE for 3-Halpha and 4-Hbeta, thus clearly links the stereochemistry of the two rings.

$^{13}$C-NMR (75.47 MHz, CDCl$_3$): δ=−5,4. −4.8, −4.5 (3xq, SitBuMe$_2$), 17.9, 18.3 (2×s, SitBuMe$_2$), 25.8, 26.0 (2×q, SitBuMe$_2$), 29.3 (q, N-CH$_3$), 35.2. 41.3 42.7 (3×t, 1-C, 3-C, 6-C), 37.7, 42.9 (2×d, 3a-C, 6a-C), 56.4 (d, 4-C), 61.9 (t, 8-C), 74.4 (d, 5-C), 122.2 (d, 7-C), 128.6, 129.0 (2×d, Ar-C), 132.1 (d, Ar-C), 132.1 (d, Ar-C), 141.0 (s, Ar-C), 164.2 (s, 2-C).

MS (EI, 70 eV): m/z (%)=549 (M$^+$, 48), 492 (M$^+$-C$_4$H$_9$, 100), 246 (33), 147 (33), 131 (28), 89 (18), 75 (26), 73 (100).

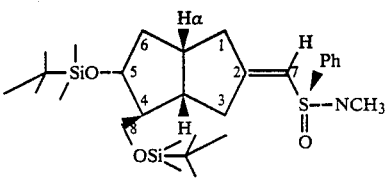

11

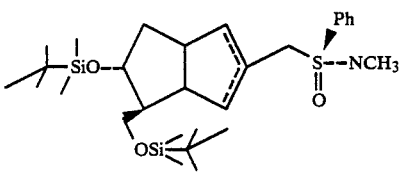

11i (9) [3aS-(2alphabeta, 3abeta, 4beta, 5alpha, 6abeta)] -5-[[(1,1-dimethylethyl)-dimethylsilyl]-oxy-4-[[[(1,1-dimethylethyl)-dimethylsilyly]-oxy]-2beta-(S)-[[N-methyl-S-phenyl)-sulfonimidoyl]-methyl]-hexahydropentalen]-2alpha(1H)-ol (12)

305 mg (1.8 mmol) of R-1 (ee is greater than or equal to 95%) is reacted according to A 1 in 20 ml of absolute THF with 715 mg (1.8 mmol) of 9. LC on 130 g of silica gel (hexane/ethyl acetate 3:1) yields 960 mg (94%) of 12 as colorless oil, which only slowly crystallizes in the refrigerator, melting point 67°–68° C., [α]$_D^{20}$=−42°, [α]$_{546}^{20}$=−50° (c=1 in acetone); 10 and 12 can be distinguished by thin-layer chromatography by repeated development with hexane/ethyl acetate 6:1, 10 is more polar than 12.

C$_{29}$H$_{53}$NO$_4$SSi$_2$ cal. C 61.33, H 9.41, N 2.47; fnd. C 61.55, H 9.72, N 2.39.

(567.99)

$^1$H-NMR (300 MHz, CDCl$_3$): δ=0.0, 0.01, 0.02 (2×s, 6H und s, 6H, SitBuMe$_2$), 0.85, 0.87 (2×s, 18H, SitBuMe$_2$), 1.68 (dd, 1H, J$_{1\beta/1a}$=13 Hz, J$_{1\beta/6a\beta}$=8 Hz, 1- oder 3-H$\beta$ und ddd, 1H, J$_{6a/6\beta}$=13 Hz, J$_{6/6a\beta}$=8 Hz, J$_{6/5\beta}$=5.5 Hz, 6-H), 1.88 (dd, 1H, J$_{1a/1\beta}$=13 Hz, J$_{1a/6a\beta}$=5 Hz, 1- oder 3-H$_a$), 1.98 (m, 1H, 4-H), 1.96–2.14 (dd, 1H, J$_{3\beta/3a}$=13 Hz, J$_{3\beta/3a\beta}$=7 Hz, 3-oder 1-H$\beta$), 2.0–2.22 (2×m, 2H, 6-H, 3a-H$\beta$), 2.34–2.50 (m, 1H, 6a-H$\beta$ und dd, 1H, 3-oder 1-Ha), 2.60 (s, 3H, N-CH$_3$), 3.06 (d, 1H, J=14 Hz, 7-H), 3.43 (d, 1H, J=14 Hz, 7-H), 3.50 (dd, 1H, J=11 Hz, J$_{8/4a}$=5.5 Hz, 8-H), 3.62 (dd, 1H, J=11 Hz, J$_{8/4a}$=4 Hz, 8-H), 3.83 (dt, 1H, J$_{5\beta/4a}$=7

Hz, $J_{5\beta/6}=5.5$ Hz, 5-H$\beta$), 6.42 (s, broad, 1H, -OH), 7.50–7.66 (m, 3H, Ar-H), 7.80–7.92 (m, 2H, Ar-H).

$^{13}$C-NMR (75.47 MHz, CDCl$_3$): $\delta = -5.6, -5.3, -4.7, -4.3$ (4×q, SitBuMe$_2$), 18.2, 18.5 (2×s, SitBuMe$_2$), 18.2, 18.5 (2×s, SitBuMe$_2$), 26.6, 26.1 (2×q, SitBuMe$_2$), 28.9 (q, N-CH$_3$), 38.4, 41.4 (2×d, 3a-C, 6a-C), 41.9, 45.4, 46.9 (3×t, 1-C, 3-C, 6-C), 56.7 (d, 4-C), 63.4, 64.6 (2×6, 7-C, 8-C), 75.5 (d, 5-C), 82.2 (s, 2-C), 129.1, 129.6 (2×d, Ar-C), 132.9 (d, Ar-C), 140 (s, Ar-C).

MS (EI, 70 eV): m/z (%)=567 (M$^+$, 2), 552 (M$^+$ −15.5), 510 (M$^+$-C$_4$H$_9$, 53), 341 (29), 223 (19), 156 (42), 147 (50), 125 (23), 73 (40), 69 (30), 56 (100), 41 (73).

MS (FD): m/z=568 (M$^+$ +1), 567 (M$^+$), 510 (M$^+$-C$_4$H$_9$).

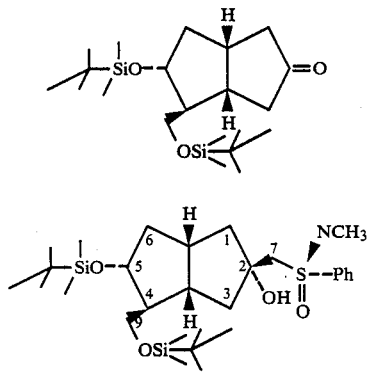

(10) [3aS-(2E,3aalpha,4alpha,5beta,6aalpha)]-S(S)-[5-[[(1,1-dimethylethyl)-dimethylsilyl]-oxy]-4-[[[(1,1-dimethylethyl)-dimethylsilyl]-oxy]-methyl]-hexahydro-2(1H)-pentalenoylidene]-methyl-N-methyl-S-phenyl]-sulfoximine (13)

595 mg (1.05 mmol) of 12 is reacted according to A 2 in 30 ml of absolute THF. LC on 100 g of silica gel (hexane/ethyl acetate 1:1) yields 525 g (91%) of 13 as colorless oil, which crystallizes in the refrigerator, melting point below room temperature, $[\alpha]_D^{20} = +59°$, $[\alpha]_{546}^{20} = +71°$ (c=0.39 in acetone).

In contrast with example 8 in the $^1$H-NMR (300 MHz) of 13 no trace of an isomerization is to be seen. 11 and 13 can also be distinguished by thin-layer chromatography, and 11 is more polar than 13.

C$_{29}$H$_{51}$NO$_3$SSi$_2$ cal. C 63.33, H 9.35, N 2.55; fnd. C 63.04, H 9.44, N 2.34.

$^1$H-NMR (300 MHz, CDCl$_3$): $\delta = 0.01, 0.02, 0.08$ (1×s, 6H, 2×s, 6H, SitBuMe$_2$), 0.86, 0.87 (2×s, 18H, SitBuMe$_2$), 1.26 (dt, 1H, $J_{6a/6\beta}=13$ Hz, $J_{6/6aa}=J_{6/5a}=7.5$ Hz, 6-H), 1.53 (ddt, 1H, $J_{4\beta/5a}=J_{4\beta/3aa}=7.5$ Hz, $J_{4\beta/8}=6$ Hz, $J_{4\beta/8}=4$ Hz, 4-H$\beta$), 2.08 (dt, 1H, $J_{6a/6\beta}=13$ Hz, $J_{6/6aa}=J_{6/5a}=7.5$ Hz, 6-H), 2.21 (dq, 1H, $J_{3aa/6aa}=J_{3aa/4\beta}=J_{3aa/3a}=7.5$ Hz, $J_{3aa/3\beta}=3$ Hz, 3a-Ha), 2.37 (m, 1H, $J_{6aa/3aa}=J_{6aa/6a}=J_{6aa/6\beta}=7.5$ Hz, $J_{6aa/12}=3$ Hz, $J_{6aa/1\beta}=2$ Hz, 6a-Ha), 2.24–2.65 (m, 3H, 1-Ha, 3-Ha, 3-H$\beta$), 2.65 (s, 3H, N-CH$_3$), 2.87 (dd, 1H, $J_{1\beta/1a}=18$ Hz, $J_{1\beta/6aa}=3$ Hz, 1-H$\beta$), 3.50 (dd, 1H, J=11 Hz, J=6 Hz, 8-H), 3.59 (dd, 1H, J=11 Hz, J=4 Hz, 8-H), 3.83 (q, 1H, J=7.5 Hz, 5-HA), 6.24 (s, breit, 1H, 7-H), 7.42–7.56 (m, 3H, Ar-H), 7.80–7.90 (m, 2H, Ar-H).

Allocation of the double bond configuration is clearly performed by uncoupling or 2D-$^1$H measurement. By uncoupling in the case of 4-H the bridgehead of 3a-H can be clearly identified. Now if irradiation takes place in the case of 1-Hbeta, which because of its deep field shift or the double bond cis must be allocated to the sulfoximine function, only the signal is simplified, which is allocated to the bridgehead of 6a-Halpha. The signal 3a-Halpha does not change. The 2D measurement estabishes the allocation (performed by S. Braun, Darmstadt).

$^{13}$C-NMR (75.47 MHz, CDCl$_3$): $\delta = -5.5, -5.4, -4.9, -4.4$ (4×q, SitBuMe$_3$), 18.0, 18.3 (2×s, SitBuMe$_2$), 25.8, 25.9 (2×q, SitBuMe$_2$), 29.3 (q, N-CH$_3$), 36.5, 39.5, 41.3, 41.6, 41.7 (2×d, 3×t, 1-C, 3-C, 6-C, 3a-C, 6a-C), 55.8 (d, 4-C), 62.6 (t, 8-C), 74.4 (d, 5-C), 122.3 (d, 7-C), 128.6, 129.0 (2×d, Ar-C), 132.1 (d, Ar-C), 141.0 (s, Ar-C), 164.1 (s, 2-C).

MS (EI, 70 eV): m/z (%)=549 (M$^+$, 50), 534 (M$^+$ −15.8), 492 (M$^+$-C$_4$H$_9$, 100), 147 (56), 131(23), 89(23), 73(100).

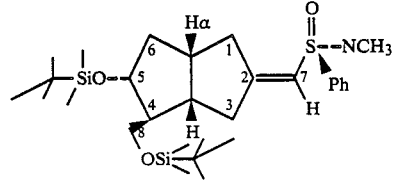

Synthesis of alkene 5a from sulfoximine 3.

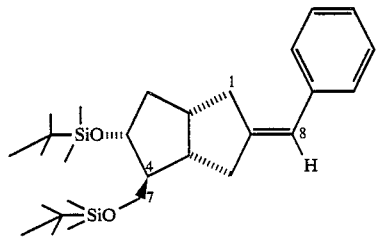

To a solution of sulfoximine 3 (110 mg, 0.20 mmol) and NiCl$_2$(dppp) (5.42 mg, 0.01 mmol, 5 mol%) in 10 ml dry ether was added at 0° C. under dry nitrogen a solution of 4a/2 MgX$_2$ (0.8 ml of 1.0M in ether, 0.8 mmol) [this reagent can be prepared either in situ by the addition of a solution of ZnCl$_2$ (8.5 ml of 4.32M in ether, 36.7 mmol) to a solution of 9a (24.5 ml of 3.0M in ether, 73.4 mmol) and refluxing for 1 h or by adding to a solution of sublimed Ph$_2$Zn (0.5M in ether) 2 equiv. of MgBr$_2$.Et$_2$O]. The resulting mixture was heated to reflux for 24 h followed by quenching with 10 ml saturated NH$_4$Cl solution. Extraction with n-hexane, drying of the combined extracts with MgSO$_4$, filtration over silica gel, evaporation of solvents, and chromatography (MPLC, silica gel, 1. n-hexane-ethyl acetate 9:1, 2. n-hexane-THF 300:1) of the residue gave alkene 5a (78.5 mg, 83%) as colourless oil; 99:1 ds [determined by $^1$H NMR (400 MHz) and $^{13}$C NMR (100 MHz), see manuscript footnote 17], $[\alpha]_{305}^{20} + 20.5°$ (c 0.2, n-hexane).

$^1$H NMR (400 MHz, CDCl$_3$) $\delta$ −0.01, 0.00, 0.04, 0.06 (s, SitBuMe$_2$, 12H), 0.83, 0.89 (s, SitBuMe$_2$, 18H), 1.21 (ddd, J=12 Hz, 9 Hz, 8 Hz, 6-H, 1H), 1.52 (dddd, J=9 Hz, 7 Hz, 5 Hz, 4 Hz, 4-H$\beta$, 1H), 2.10 (ddd, J=12 Hz, 9 Hz, 7 Hz, 6-H, 1H), 2.25 (dq, J=9 Hz, 4 Hz, 3a-H, 1H), 2.35–2.75 (m, 1-H, 3-H, 6a-H, 5H), 3.58 (dd, J=10 Hz, 5 Hz, 7-H, 1H), 3.67 (dd, J=10 Hz, 4 Hz, 7-H, 1H), 3.85 (dt, J=9 Hz, 7 Hz, 5-Hα, 1H), 6.33 (m, 8-H, 1H), 7.12-7.32 (m, Ph, 5H).

$^{13}$C NMR (100 MHz, CDCl$_3$) δ −5.38, −5.26, −4.74, −4.40 (s, SiMe$_2$ tBu), 18.14, 18.46 (SiMe$_2$ tBu), 25.95, 26.08 (SiMe$_2$ tBu), 37.67, 41.71, 42.40 (C-1, C-3, C-6), 39.48, 40.55 (C-3a, C-6a), 55.73 (C-4), 62.3 (C-7), 74.20 (C-5), 121.72 (C-8), 125.79, 128.13, 128.49 (Ph), 138.79 (Cipso), 146.75 (C-2).

MS (EI, 70 eV) m/z (%) 472 (M+. 7), 415 (10), 341 (5), 283 (15), 209 (64), 167 (20), 155 (59), 147 (90), 129 (26), 117 (29), 91 (47), 73 (100), 57 (30), 42 (52).

Anal. Calcd. for C$_{28}$H$_{48}$O$_2$Si$_2$: C, 71.12; H, 10.23. Found: C, 70.96; H, 10.24.

Synthesis of Z-5a

For Z-5a, which was synthesized by the above procedure from [Z,S(S)]-3, only the relevant NMR data differing from those of 5a are given.

$^1$H NMR (400 MHz, CDCl$_3$) δ 0.84 (s, 9H), 0.86 (s, 9H), 3.53 (dd, 1H), 3.61 (dd, 1H), 3.84 (dt, 1H).

$^{13}$C NMR (100 MHz, CDCl$_3$) δ 36.4, 36.9, 43.1, 43.5, 56.7.

Synthesis of alkene 5b from sulfoximine 3.

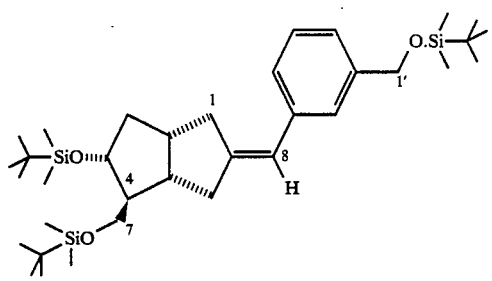

A solution of sulfoximine 3 (220 mg, 0.40 mmol) and NiCl$_2$ (dppp) (10.8 mg, 0.02 mmol, 5.4 mol %) in 10 ml dry ether was treated at 0° C. under dry nitrogen with a solution of 4b/2 MgX$_2$ (2.85 ml of 0.35M in ether, 1 mmol) [the reagent was prepared by mixing solutions of ZnCl$_2$. (1.56 ml of 4.32M in ether, 6.75 mmol) and 9b (20 ml of 0.675M in ether, 13.5 mmol), and refluxing for 1 h]. The reaction mixture was heated to reflux for 20 h, quenched with 10 ml saturated NH$_4$Cl solution and extracted with n-hexane. Drying of the combined extracts with MgSO$_4$, filtration over silica gel, evaporation of solvents, and chromatography (MPLC, silica gel, 1. n-hexane-ethyl acetate 9:1, 2. n-hexane-THF 300:1) of the residue gave alkene 5b (220 mg, 89%) as colourless oil; 99:1 ds [determined by $^1$H (400 MHz) and $^{13}$C NMR (100 MHz), see manuscript footnote 17], [α]$_{305}^{20}$+81.9 (c, 0.5 n-hexane).

$^1$H NMR (400 MHz, CDCl$_3$), δ 0.0, 0.01, 0.05, 0.01 (s, SitBuMe$_2$, 18H), 0.84, 0.90, 0.93 (s, SitBuMe$_2$, 24H), 1.21 (ddd, J=13 Hz, 10 Hz, 9 Hz, 6-Hα, 1H), 1.51 (m, 4-Hβ, 1H), 2.09 (ddd, J=13 Hz, 8 Hz, 7 Hz, 6-Hβ, 1H), 2.24 (dq, J=9 Hz, 4 Hz, 3a-H, 1H), 2.36-2.51 (m, 6a-H, 1-Hα, 1-Hβ, 3H), 2.60-2.75 (m, 1-Hβ, 3-H, 2H), 3.59 (dd, J=10 Hz, 5 Hz, 7-H, 1H), 3.66 (dd, J=10 Hz, 4 Hz, 7-H, 1H), 3.86 (dt, J=9 Hz, 7 Hz, 5-Hα, 1H), 4.72 (s, 1'-H, 2H), 6.32 (bm, 8-H, 1H), 7.07-7.28 (m, Ph, 4H).

$^{13}$C NMR (100 MHz, CDCl$_3$) δ −5.37, −5.26, −5.12, −4.73, −4.39 (SiMe$_2$ tBu), 18.1, 18.46, 18.52 (SiMe$_2$ tBu), 26.09, 25.96 (SiMe$_2$ tBu), 37.79, 41.71, 42.38 (C-1, C-3, C-6), 39.5, 40.61 (C-3a, C-6a), 55,74 (C-4), 62.35 (C-7), 65.13 (C-1'), 74.25 (C-5), 121.82 (C-8), 123.59, 126.11, 127.15, 127.99 (C-2", C-4", C-5", C-6"), 138.72, 141.22, 146.68 (C-2, C-1", C-3").

MS (EI, 70 eV) m/z (%) 616 (M+, 1), 559 (12), 484 (8), 427 (6), 352 (9), 299 (15), 295 (16), 223 (23), 221 (56), 167 (20), 147 (70), 143 (19), 141 (13), 89 (65), 73 (100).

Anal. Calcd. for C$_{35}$H$_{64}$O$_3$Si$_3$: C, 68.12; H, 10.45. Found: C, 68.16; H, 10.52.

Synthesis of Z-5b

For Z-5b, which was synthesized by the above procedure from [Z,S(S)]-3, only the relevant NMR data differing from those of 5b are given.

$^1$H NMR (400 MHz, CDCl$_3$) δ 0.85 (s, 9H), 0.87 (s, 9H), 3.57 (m, 1H).

$^{13}$C NMR (100 MHz, CDCl$_3$) δ 39.09, 39.64, 45.78, 45.99, 59.39.

Synthesis of alkene 5c from sulfoximine 3.

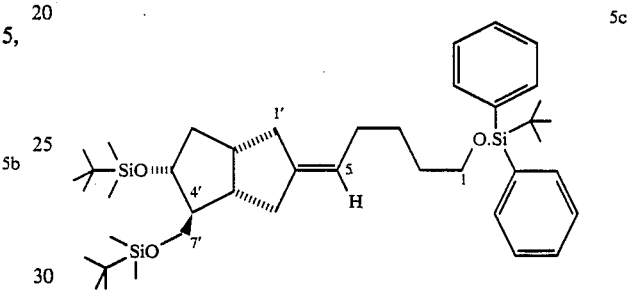

A solution of sulfoximine 3 (55 mg, 0.10 mmol) and NiCl$_2$ (dppp) (2.8 mg, 0.005 mmol, 5 mol %) in 4 ml dry ether was treated at 0° C. under dry nitrogen with a solution of 4c (1 ml of 0.34M in ether, 0.34 mmol) [salt-free 4c was prepared by dropwise addition of a solution of ZnCl$_2$ (1.75 ml of 4.32M in ether, 7.56 mmol) to a solution of 9c (Cl instead of Br) (27 ml of 0.56M in ether, 15.1 mmol), refluxing for 1 h, treatment with 30 ml n-hexane, filtration, evaporation of the solvents, and dissolution of the residue in 20 ml dry ether to give a 0.34M solution of 4c; its content was determined by quenching with CF$_3$COOD and isolation of DCH$_2$(CH$_2$)$_3$OSitBuPh$_2$ (98%, 95% D)], and with a solution of MgBr$_2$ (0.42 ml of 2.35M in ether, 0.98 mmol). The reaction mixture was stirred for 5 days at 0° C., quenched with 5 ml saturated NH$_4$Cl solution and extracted with n-hexane. The combined extracts were dried with MgSO$_4$, and filtered over silica gel. Evaporation of solvents and chromatography (MPLC, silica gel, 1. n-hexane-ethyl acetate 9:1, 2. n-hexane-ether 300:1) of the residue gave alkene 5c (49.5 mg, 70%) as a colourless oil; 99:1 ds [determined by $^1$H (400 MHz), $^{13}$C NMR (100 MHz), and HPLC, see manuscript footnote 17], [α]$_{305}^{20}$+7.9° (c 0.7, n-hexane).

$^1$H NMR (400 MHz, CDCl$_3$) δ 0.01-0.04 (s, SitBuMe$_2$, 12H), 0.85, 0.90 (s, SitBuMe$_2$, 12H), 1.05 (s, SitBuPh$_2$, 9H), 1.18 (m, 1H), 1.35-1.48 (m, 3H), 1.50-1.60 (m, 2H), 1.99-2.14 (m, 3H), 2.14-2.42 (m, 4H), 3.58 (dd, J=10 Hz, 5 Hz, 7'-H, 1H), 3.60 (dd, J=10 Hz, 4 Hz, 7'-H, 1H), 3.63 (t, J=7 Hz, 1-H, 2H), 3.84 (dt, J=9 Hz, 7 Hz, 5'-H, 1H), 5.18 (tt, J=1.5 Hz, 5-H, 1H), 7.33-7.71 (m, SitBuPh$_2$, 10H).

$^{13}$C (100 Mhz, CDCl$_3$) δ −5.39, −5.27, −4.69, −4.36 (SiMe$_2$ tBu), 18.17, 18.45, 19.32 (SiMe$_2$ tBu, SiPh$_2$tBu), 25.98, 26.08 (SiMe$_2$ tBu), 26.22 (C-3), 26.99 (SiPh$_2$ tBu), 29.22 (C-4), 32.33 (C-2), 35.49, 39.58, 42.36

(C-1', C-3', C-6'), 38.30, 41.24 (C-3'a, C-6'a), 55.71 (C-4'), 62.25 (C-7'), 63.97 (C-1), 74.04 (C-5'), 121.25 (C-5), 127.66, 129.56, 134.29, 135.68 (SitBuPh$_2$), 142.69 (C-2').

MS (CI, NH$_3$, 70 eV) m/z (%) 724 ((M+NH$_4$)$^+$, 85), 707 (M$^+$ + 1, 6), 593 (7), 575 (20), 443 (27), 411 (14), 358 (8), 317 (19), 256 (35), 206 (20), 187 (100), 164 (21), 132 (37), 90 (20).

Anal. Calcd. for C$_{42}$H$_{70}$O$_3$Si$_3$: C, 71.32; H 9.98. Found C, 71.45; H, 9.97.

Extraction of the aqueous phase several times with ethyl acetate, drying of the organic phase with MgSO$_4$, evaporation of the solvent and flash-chromatography (silica gel, ethyl acetate) of the residue gave sulfoximine H$_2$-3 (11 mg, 20%).

Synthesis of Z-5c

For Z-5c, which was synthesized by the same procedure from [Z,S(S)]-3, only the relevant NMR data differing from those of 5c are given.

$^1$H NMR (400 MHz, CDCl$_3$) δ 0.847 (s, 9H), 0.897 (s, 9H).

$^{13}$C NMR (100 MHz, CDCl$_3$) δ 34.08, 37.49, 40.99, 41.79, 42.01, 56.35, 64.02, 74.00, 121.20.

Synthesis of sulfoximine H$_2$-3 from sulfoximine 3.

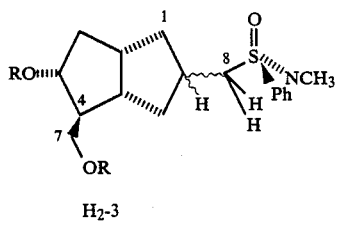

H$_2$-3

A solution of sulfoximine 3 (55 mg, 0.10 mmol) and NiCl$_2$ (dppp) (4.8 mg, 0.008 mmol, 8.8 mol %) in 5 ml dry ether was treated under dry nitrogen with a salt-free solution of 4c (1 ml of 0.34M in ether, 0.34 mmol). The reaction mixture was heated to reflux for 24 h, quenched with 5 ml saturated NH$_4$Cl solution and extracted with ethyl acetate. The combined extracts were dried with MgSO$_4$, filtered over silicagel. Evaporated of solvents and flash-chromatography (silica gel, ethyl acetate) of the residue gave H$_2$-3 (41 mg, 74%) (6–7:1 diastereomeric mixture) as colourless oil from which the major diastereomer could be separated by MPLC (silica gel, ethyl acetate); [α]$_{305}^{20}$ −141.6° (c 0.3, acetone).

$^1$H NMR (400 MHz, CDCl$_3$) δ 0.01 (s, SitBuMe$_2$, 12H), 0.83, 0.85 (s, SitBuMe$_2$, 18H), 1.07 (ddd, J=12 Hz, 10 Hz, 9 Hz, 6-Hα, 1H), 1.12 (dt, J=12 Hz, 8 Hz, 1-Hα/3-Hα, 1H), 1.26 (dt, J=12 Hz, 8 Hz, 1-Hα/3-Hα, 1H), 1.34 (dddd, J=9 Hz, 8 Hz, 5 Hz, 4 Hz, 4-Hβ, 1H), 1.78 (dd, J=12 Hz, 6 Hz, 1-Hβ/3-Hβ, 1H), 1.98 (ddd, J=12 Hz, 8 Hz, 6 Hz, 6-Hβ, 1H), 2.22 (m, 3a-H, 6a-H, 2H), 2.49 (m, 2-Hα, 1H), 2.62 (s, NMe, 3H), 3.07 (dd, J=14 Hz, 7 Hz, 8-H, 1H), 3.28 (dd, J=14 Hz, 6 Hz, 8-H, 1H), 3.55 (dd, J=10 Hz, 5 Hz, 7-H, 1H), 3.60 (dd, J=10 Hz, 4 Hz, 7-H, 1H), 3.68 (dt, J=9 Hz, 6 Hz, 5-Hα, 1H), 7.50–7.87 (m, Ph, 5H).

$^{13}$C NMR (100 MHz, CDCl$_3$) δ −5.42, −5.29, −4.76, −4.35 (SiMe$_2$ tBu), 18.15, 18.43 (SitBuMe$_2$), 25.96, 26.06 (SitBuMe$_2$), 29.59 (NMe), 32.59, 37.41, 39.15, 39.56, 42.01 (C-1, C-3, C-3a, C-6, C-6a), 40.82 (C-2), 55.99 (C-4), 61.55, 61.99 (C-7, C-8), 73.01 (C-5), 129.39, 129.45, 132.77, 138.71 (Ph).

MS (EI, M$^+$) calcd. for C$_{29}$H$_{53}$O$_3$NSSi$_2$ 551.3300, obsd. 551.3314.

MS (EI, 70 eV) m/z (%) 551 (M$^+$, 1), 495 (12), 494 (M$^+$-C$_4$H$_9$, 31), 212 (50), 209 (16), 156 (20), 149 (15), 147 (62), 135 (11), 134 (12), 133 (100), 131 (13), 125 (19), 107 (22), 105 (19), 91 (64), 89 (29), 79 (18), 75 (31), 73 (74), 67 (13).

Synthesis of alkene 5a/Z-5a from magnesio sulfoximine 8

A solution of the sulfoximine 3 (55 mg, 0.10 mmol) in 5 ml dry ether was treated at 0° C. under dry nitrogen with a solution of 9a (0.135 ml of 3.0M in ether, 0.40 mmol) for 3 h at 0° C. [(D)-3 with 100% D incorporation at C-8 as a E/Z-mixture (1:1) could be isolated in 95% yield by quenching the reaction mixture with CF$_3$COOD at this point]. The reaction mixture was transferred through a syringe needle to a suspension of NiCl$_2$ (dppp) (2.3 mg, 0.004 mmol, 4.2 mol %) in 2 ml ether. Further stirring for 3 h at 0° C., followed by usual work-up (see synthesis of 5a) gave alkene 5a (37.8 mg, 80%) as 1:1 mixture of E and Z isomers as determined by $^1$H and $^{13}$C NMR spectroscopy. Deuterative work-up gave (D)-5a with 100% D incorporation at C-8 as E/Z-mixture (1:1).

Synthesis of alkene 7 from sulfoximine 6

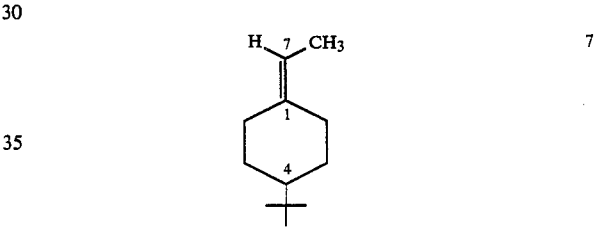

To a solution of sulfoximine 6 (155 mg, 0.50 mmol) and NiCl$_2$ (dppp) (9.8 mg, 0.018 mmol, 3.6 mol %) in 10 ml dry ether were added at 0° C. under dry nitrogen a solution of ZnMe$_2$ (1 ml of 2.1M in dichloromethane, 2.1 mmol), and a solution of MgBr$_2$ (1.8 ml of 2.35M in ether, 4.23 mmol). The reaction mixture was stirred for 5 days at 0° C., quenched with 5 ml 2N HCl and extracted with n-hexane. The combined extracts were dried with MgSO$_4$ and filtered over silica gel. Concentrated by rotatory evaporation of solvents and chromatography (MPLC, silica gel, n-hexane) of the residue gave alkene 7 (61.4 mg, 74%) as colourless liquid; bp 100° C. (20 mmHg), [α]$_{546}^{20}$ +18.7° (c 0.7, CHCl$_3$).

$^1$H NMR (400 MHz, CDCl$_3$) δ 0.825 (s, tBu, 9H), 0.865 (dq, J=4 Hz, J=13 Hz, 3-Hax, 1H), 1.04 (dq, J=4 Hz, J=13 Hz, 5-Hax, 1H), 1.15 (tt, J=13 Hz, 4 Hz, 4-Hax, 1H), 1.55 (dt, J=7 Hz, J=1.5 Hz, Me, 3H), 1.625 (m, 2-Hax, 1H), 1.80 (m, 5-Heq, 1H), 1.84 (m, 3-Heq, 1H), 1.96 (m, 6-Hax, 1H), 2.20 (dq, J=13 Hz, J=3 Hz, 6-Heq, 1H), 2.65 (dq, J=13 Hz, J=3 Hz, 2-Heq, 1H), 5.11 (tq, J=7 Hz, J=1.5 Hz, 7-H, 1H).

$^{13}$C NMR (100 MHz, CDCl$_3$) δ 12.75 (tBu), 27.74 (tBu), 28.12, 28.33, 29.28, 37.05 (C-2, C-3, C-5, C-6), 32.56 (C-4), 114.77 (C-7), 140.20 (C-1).

MS (EI, 70 eV) m/z (%) 166 (M$^+$, 40), 151 (10), 123 (30), 110 (57), 109 (54), 95 (43), 82 (34), 81 (100), 79 (39), 67 (100), 57 (100), 55 (55), 53 (34), 43 (37).

Anal. Calcd. for C$_{12}$H$_{22}$: C, 86.66; H, 13.33. Found: C, 86.48; H, 13.09

Extraction of the aqueous phase several times with ethyl acetate, drying of the organic phase with MgSO4, evaporation of the solvent, flash-chromatography (silica gel, ethyl acetate), evaporation of solvent and kugelrohrdestillation gave (+)-(S)-N-methyl-S-phenylsulfinamide (69 mg, 89%) as colourless oil which slowly crystallizes; $[\alpha]_D^{20} +169°$ (c 0.2, acetone).

Synthesis of alkene 11c from sulfoximine 11a

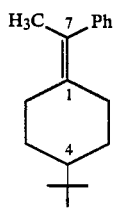

A solution of sulfoximine 11a (47.8 mg, 0.15 mmol) and NiCl2 (dppp) (2.8 mg, 0.005 mmol, 3.4 mol %) in 5 ml dry ether was treated at 0° C. under dry nitrogen with a solution of 9a (0.6 ml of 3.0M in ether, 0.60 mmol). After stirring for 3 h at 0° C. the reaction mixture was quenched with 5 ml saturated NH4Cl solution. Extraction with n-hexane, drying of the combined extracts with MgSO4, filtration over silica gel, evaporation of the solvent, and chromatography (MPLC, silica gel, n-hexane) gave alkene 11c (29 mg, 80%) as a colourless liquid; bp 140° C. (0.1 mmHg), $[\alpha]_{385}^{20} +149.6°$ (c 0.8, CHCl3), 1H NMR (400 MHz, CDCl3) δ 0.875 (s, tBu, 9H), 0.963 (dq, J=13 Hz, 4 Hz, 3-Hax/5-Hax, 1H), 1.10 (dq, J=13 Hz, 4 Hz, 3-Hax/5-Hax, 1H), 1.20 (tt, J=13 Hz, 4 Hz, 4-Hax, 1H), 1.60–2.03 (m, 4H), 1.96 (m, Me, 3H), 2.42 (dq, J=13 Hz, J=3 Hz, 6-Heq, 1H), 2.84 (dq, J=13 Hz, J=3 Hz, 2-Heq, 1H), 7.13 (m, Ho, 2H), 7.20 (m, Hp, 1H), 7.31 (m, Hm, 2H).

13C NMR (100 MHz, CDCl3) δ 20.32 (tBu), 27.73 (tBu), 28.75, 29.15, 30.53, 31.79 (C-2, C-3, C-5, C-6), 32.54 (C-4), 48.44 (Me), 125.77, 126.81, 128.01, 128.54 (Ph) 135.44 (C-7), 145.37 (C-1).

MS (EI, 70 eV) m/z (%) 243 (M+ +1, 14), 242 (M+, 64), 185 (13), 171 (11), 157 (13), 144 (19), 143 (48), 141 (15), 137 (19), 131 (23), 129 (64), 128 (36), 118 (76), 115 (25), 106 (21), 105 (89), 91 (50), 81 (28), 77 (28), 67 (22), 57 (100), 51 (16), 41 (36).

MS (EI, M+) calcd. for C18H26 242.2041, obsd. 242.2047.

Stereoselective Synthesis of Carbacyclins

Asymmetric synthesis of alkyl and aryl substituted exocylic alkenes from ketones[1] still constitutes a challenge despite some success achieved recently through Wittig-type olefinations.[2,3] The synthesis of carbacyclins 1 from the key intermediate 2[2b,4] represents a most sought after case; thus, the method of this invention is of high practical importance. Previous syntheses of 1 from 2[4] have failed to stereoselectively effect the geometry of the exocyclic double bond.[5]

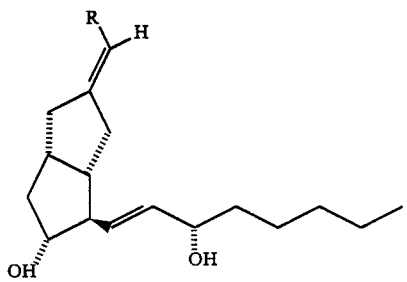

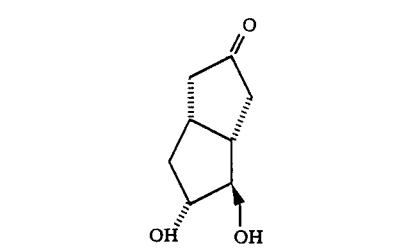

a: R = m-C6H4COOH
b: R = (CH2)3CO2H

Transition metal catalyzed cross-coupling of alkenyl halides,[6] sulfones,[7a] sulfides,[6] selenides,[6] phosphates,[7b] ethers[6] or triflates[6] ought to be a most promising method therefor, given such derivatives can be prepared from ketones, e.g. 2, in a stereocontrolled manner which is, unfortunately, not the case.[8] However, alkenyl sulfoximines 3 and 6, e.g., are obtained with high diastereoselectivity (ds) from 2 and t-butylcyclohexanone, respectively, and enantiomerically pure LiCH2SO(N-Me)Ph[9] via asymmetric elimination.[10]

This invention achieves a E-selective synthesis of exocyclic alkenes 5, ultimate precursors for 1,[11,12] from 3 by Ni-catalyzed cross-coupling with diorganozinc reagents 4 (+salt) and the synthesis of optically active alkenes 7 and 11c from 6 and 11a, respectively. There has further been discussed a Ni-catalyzed cross-coupling between α-magnesio alkenyl sulfoximine 8 and organomagnesiums 9 giving alkenyl magnesium derivatives 10.

Scheme I

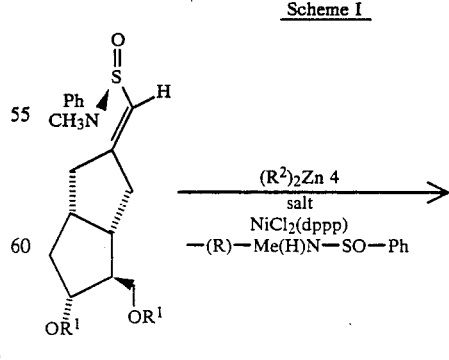

R1 = SitBuMe2
R3 = SitBuPh2

-continued
Scheme I

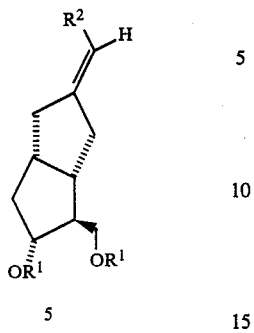

5 a: $R^2$ = Ph
b: $R^2$ = m-$C_6H_4CH_2OR^1$
c: $R^2$ = $(CH_2)_4OR^3$

Cross-coupling of 3 with pure 4a in the presence of $MgBr_2$ (1 equiv), LiBr (1 equiv) or $ZnCl_2$ (2 equiv) and $NiCl_2$ (dppp), dppp=$Ph_2P(CH_2)_3PPh_2$, as catalyst proceeded in ether at reflux (24 h) to give the aryl alkene 5a[13] in 83% yield and 99:1 ds (Scheme I).[14] It is to be noted that without magnesium, lithium or zinc salts as cocatalysts practically no coupling occurs.[15] Starting from pure 4a and adding one of the above salts is no prerequisite to the success of the coupling reaction. An etheral solution of 4a (+2 $MgX_2$), prepared in situ from Grignard reagent 9a and $ZnCl_2$. $Et_2O$ (molar ratio of 2:1), may be used instead with equal success. In a like manner the aryl carbacyclin precursor 5b[13] was synthesized from 3 and the diaryl zinc derivative 4b (+2 $MgX_2$) in 89% yield and 99:1 ds.

Extending the coupling of 3 with arylzinc derivatives 4a,b to that with dialkylzinc derivative 4c was met with success, too. Thus, reaction of 3 with 4c (+2 $MgX_2$) in ether in the presence of $NiCl_2$ (dppp) as described above gave a 70% yield of alkyl carbacyclin precursor 5c[13] in 99:1 ds. Here as byproduct reduced 3, $H_2$-3, easily separable from 5c by chromatography, was formed in 20% yield. Attempted coupling of 3 with salt free 4c[16] led to $H_2$-3 in 74% yield without formation of 5c. Z isomers of 5a–c were obtained stereoselectively from the Z,S(S) isomer of 3[10] and 4a–c by the above protocol. In comparison of 5a–c with their Z isomers, the ds of the coupling reactions was unequivocally ascertained.[17] The cross-coupling was further extended to the synthesis of enantiomerically pure alkene 7[8b,13] from (+)-6[10] and $Me_2Zn$ in the presence of $MgBr_2$ (2 equiv) which could be accomplished in 74% yield (Scheme II). Besides 5a–c and 7 optically active MeN(H)-SO-Ph[18] ($\geq$98% ee) is formed in high yields with retention of configuration.

Scheme II

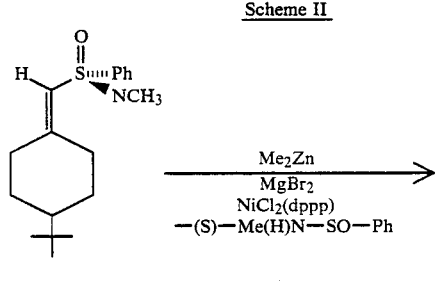

6

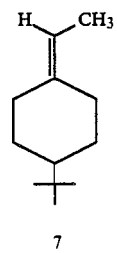

7

The role of the metal salts in the above cross-couplings with diorganozincs is not clear at present.[15] However, that even $ZnCl_2$ causes a dramatic rate enhancement is noteworthy.

Coupling of 3 with more basic organomagnesiums or -lithiums takes a different and surprising course. 3 (1 equiv) undergoes a $NiCl_2$ (dppp) (8 mol %) catalyzed coupling with 9a–c (3 equiv, ether, 0° C., 3 h) to give 5a (74%), 5b (75%), and 5c (27%) with complete loss of olefinic stereochemistry (Scheme III).[19] Deuteration experiments revealed that (a) 3 is quantitatively metallated even at −78° C. in 8-position by 9a and presumably also by 9b and 9c (Cl instead of Br) furnishing β-metallated alkenyl sulfoximine 8 which isomerises at 0° C. to a 1:1 mixture of 8 and its Z isomer[20] and (b) a facile Ni-catalyzed cross-coupling of 8 (E:Z=1:1) with 9a–c (ether, 0° C., 3 h) occurs to give the alkenyl metal derivatives 10a–c and their Z isomers (1:1).[21]

Scheme III[a]

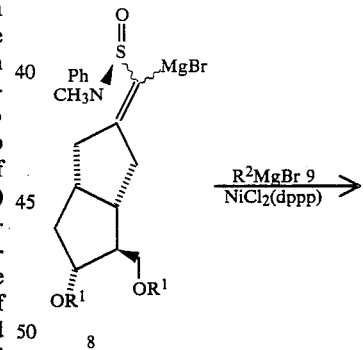

8

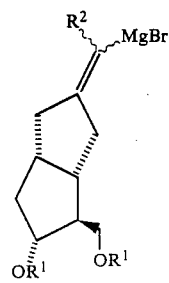

10 a: $R^2$ = Ph
b: $R^2$ = m-$C_6H_4CH_2OR^1$
c: $R^2$ = $(CH_2)_4OR^3$

-continued
Scheme III[a]

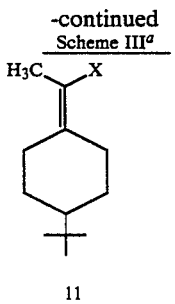

11 a: X = SO(NMe)Ph
b: X = MgBr
c: X = Ph

[a]For R[1], R[3] see Scheme I

Two conceivable alternative routes to 10 from 8 have been excluded by showing that under the reaction conditions (a) 5a is not metallated at the double bond by 9a to give 10a, and (b) alkenyl sulfoximine 11a as a model compound suffers no cleavage to the alkenyl Grignard derivative 11b upon treatment with 9a in the presence of NiCl$_2$ (dppp). Instead, a cross-coupling between 11a and 9a took place which led to the isolation of optically active disubstituted exocyclic alkene 11c[13] in 80% yield.

The above described Ni-catalyzed cross-coupling of a α-functionalized alkenyl metal derivative with organometallics to give substituted alkenyl metal derivatives is without precedent.[6]

The chemistry illustrated above is routinely applicable to preparation of a wide variety of carbacyclin-type compounds having pharmacological activity by straightforward analogy to the foregoing and for all products of the process of this invention, e.g., cross-couplings of alkenyl and α-metallo alkenyl sulfoximines, e.g., applied to 3-oxa-carbacyclin.[2b,c]

Literature
(1) Bestmann, H. J.; Lienert, J. Angew. Chem. Int. Ed. Engl. 1970, 9, 796. Bestmann, H. J.; Heid, E.; Ryschka, W.; Lienert, J. Liebigs Ann. Chem. 1974, 1684.
(2) (a) Hanessian, S.; Delorme, D.; Beaudoin, S.; Leblanc, Y. J. Am. Chem. Soc. 1984, 106, 5754. (b) Gais, H.-J.; Schmiedl, G.; Ball, W. A.; Bund, J.; Hellmann, G.; Erdelmeier, I. Tetradedron Lett. 1988, 29, 1773. (c) Rehwinkel, H.; Skupsch, J.; Vorbrüggen, H. Tetrahedron Lett. 1988, 29, 1775.
(3) Also, see: Duhamel, L.; Ravard, A.; Plaquevent, J.-C.; Davoust, D. Tetrahedron Lett. 1987, 28, 5517. Fiaud, J. C.; Legros, J. Y. Tetrahedron Lett. 1988, 29, 2959.
(4) 1a,[4a] 1b[4b] and analogues[2b,c] are showing great promise as therapeutic agent for circulatory diseases: (a) Flohe, L.; Böhlke, H.; Frankus, E.; Kim, S. M., A.; Lintz, W.; Loschen, G.; Michel, G.; Müller, B.; Schneider, J.; Seipp, U.; Vollenberg, W.; Wilsmann, K. Arzneim.-Forsch./Drug Res. 1983, 33, 1240. (b) Nickolson, R. C.; Town, M. H.; Vorbrüggen, H. Med. Res. Rev. 1985, 5, 1 and literature cited therein.
(5) For alternative E-selective syntheses of carbacyclins not starting from 2 or its derivatives, see: Sodeoka, M.; Satoh, S.; Shibasaki, M. J. Am. Chem. Soc. 1988, 110, 4823. Shibasaki, M.; Sodeoka, M.; Ogawa, Y. J. Org. Chem. 1984, 49, 4098. Hutchinson, D. K.; Fuchs, P. L. J. Am. Chem. Soc. 1987, 109, 4755.
(6) For pertinent reviews, see: Kumada, M. Pure Appl. Chem. 1980, 52, 669. Negishi, E. Acc. Chem. Res. 1982, 15, 340. Trost, B. M.; Verhoeven, T. R. In Comprehensive Organometallic Chemistry; Wilkinson, G; Stone, F. G. A.; Abel, E. V., Ed.; Pergamon Press: Oxford; 1982; Vol 8, p 799. Jolly, P. W. In Comprehensive Organometallic Chemistry; Wilkinson, G; Stone, F. G. A.; Abel, E. V., Ed.; Pergamon Press: Oxford; 1982; Vol 8, p 713. Poetsch, E. Kontakte (Darmstadt) 1988, 2, 15.
(7) (a) Alvarez, E.; Cuvigny, T.; Herve du Penhoat, C.; Julia, M. Tetrahedron 1988, 44, 111 and earlier work cited therein. (b) Hayashi, T.; Fujiawa, T.; Okamoto, Y.; Katsuro, Y.; Kumada, M. Synthesis 1981, 1001.
(8) For enantioselective synthesis of cyclohexylidene bromomethanes from cyclohexyl methylmagnesium bromides,[8a] and cross-coupling[8a,b] of the former, see: (a) Solladie, G.; Zimmermann, G. Tetrahedron Lett. 1984, 25, 5769. (b) Duraisamy, M.; Walborsky, H. M. J. Am. Chem. Soc. 1984, 106, 5035.
(9) Gais, H.-J.; Erdelmeier, I.; Lindner, H. J.; Vollhardt, J. Angew. Chem. Int. Ed. Engl. 1986, 25, 938. Johnson, C. R.; Schroeck, C. W.; Shanklin, J. R. J. Am. Chem. Soc. 1973, 95, 7424.
(10) Erdelmeier, I.; Gais, H.-J.; Lindner, H. J. Angew. Chem. Int. Ed. Engl. 1986, 25, 935 and further examples described therein.
(11) Konishi, Y.; Kawamura, M.; Iguchi, Y.; Arai, Y.; Hayashi, M. Tetrahedron 1981, 37, 4391.
(12) For selective deprotection of silyl ethers[12a] as well as oxidation of hydroxymethyl groups[12b], see: (a) Cunico, R. F.; Bedell, L. J. Org. Chem. 1980, 45, 4797. (b) Adler, E.; Becker, H. D. Acta Chem. Scand. 1961, 15, 849.
(13) Optical rotations, $[\alpha]_{385}^{20}$, for compounds prepared in this study are as follows; 5a, +20.5° (c 0.20, n-hexane); 5b, +81.9 (c 0.5, n-hexane); 5c, +7.9° (c 0.7, n-hexane); 7, +18.7° (c 0.7, CHCl$_3$) (=546 nm); 11c, +149.6° (c 0.8, CHCl$_3$).
(14) With PdCl$_2$(PPh$_3$)$_2$ under identical conditions no coupling occurred.
(15) For double metal catalysis and salt effects in cross-coupling reactions, see: Negishi, E.; Okukado, N.; King, A. O.; Van Horn, D. E.; Spiegel, B. I. J. Am. Chem. Soc. 1978, 100, 2254. Normant, J. F. In Modern Synthetic Methods; Scheffold, R., Ed.; Salle-Sauerländer: Frankfurt; 1983; Vol. 3, p,139. Scott, W. J.; Crisp, G. T.; Stille, J. K. J. Am. Chem. Soc. 1984, 106, 4630.
(16) Salt free 4c in ether was prepared from 9c (Cl instead of Br) and ZnCl$_2$. Et$_2$O (molar ratio 2:1), precipitation of the salts by addition of n-hexane, filtration, evaporation, and dissolution in ether.
(17) E/Z ratios were determined by HPLC (two 10 cm×0.8 cm 4μ-C$_{18}$-columnes (waters): solvent, 97:3 methanol/water; flow rate, 1.7 ml/min; detection, UV (225 nm) (for 5c) and $^1$H NMR (400 MHz) using the signals of the SitBuMe$_2$ groups (5a: 0.83, 0.89, Z isomer: 0.84, 0.86; 5b: 0.84, 0.90, 0.93, Z isomer: 0.85, 0.87; 5c: 0.850, 0.900, Z isomer: 0.847, 0.897).
(18) Johnson, C. R.; Jonsson, E. V.; Wambsgans, A. J. Org. Chem. 1979, 44, 2061.

(19) Cross-coupling of 3 with 9a–c (THF, 0° C., 30 min) in the presence of stoichiometric amounts of Fe(acac)$_3$[78] gave 5a (74%, E:Z=4:1), 5b (75%, E:Z=3:1), and 5c (34%, E:Z=7:1), respectively.

(20) α-Metallated alkenyl sulfoximines, e.g. 8, accessible by metallation of corresponding alkenyl sulfoximines with organo-magnesiums or -lithiums are configurationally stable at −78° C. and can be alkylated with retention of configuration (e.g. 11a): Gais, H.-J.; Erdelmeier, I.; Diederichsen, U., manuscript in preparation.

(21) (D)-3 (95%, 100% D, E:Z=1:1) and (D)-5a (80%, 100% D, E:Z=1:1) were isolated from 8 and 10a, respectively, through CF$_3$COOD quench followed by usual work-up.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the production of an unsymmetrical olefin of formula I

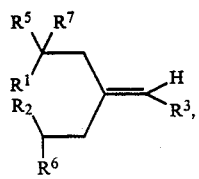

wherein
R$^1$ and R$^2$ are a common bond or the radical

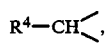

R$^3$ is the group

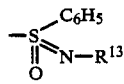

R$^4$ is a straight-chain or branched chain alkyl radical with 1–10 C atoms,

R$^5$ and R$^6$ are the same or different and are hydrogen, alkyl with 1–10 C atoms, cycloalkyl with 5–7 C atoms, alkoxy with 1–6 C atoms, aryl with 6–10 C atoms aralkyl with 7–12 C atoms or a 5–7 -membered heterocycle, which can contain another N, O or S atom, or, if R$^1$ and R$^2$ represent a common bond, R$^5$ and R$^6$ jointly are the radical

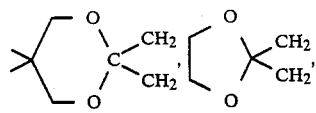

-continued

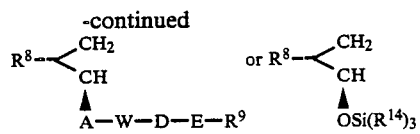

R$^8$ is hydrogen, alkyl with 1–10 C atoms or OR$^{10}$, wherein

R$^{10}$ is hydrogen or a silyl, ether or acid radical,

A is a trans—CH=CH— group or a —C≡C— group,

W is hydroxymethylene or a —C(CH$_3$)(OH)— group,

D is an alkylene group with 1–5 C atoms,

E is a —C≡C— or —CH=CR$^{11}$— group,

R$^9$ is an alkyl group with 1–6 C atoms, or DER$^9$ together are a cycloalkyl group with 5–6 C atoms or the radical

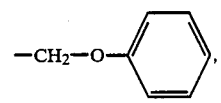

R$^{11}$ is alkyl with 1–4 C atoms,

R$^7$ is hydrogen or the radical —(CH$_2$)$_m$—R$^{12}$ or —(CH$_2$)$_{m-o}$—(Z$_1$—(CH$_2$)$_{m-p}$)$_x$—(Z$_2$—(CH$_2$)$_{m-q}$)$_y$—R$^{12}$, R$^{13}$ is alkyl with 1–4 C atoms or a tosyl radical, R$^{14}$ is alkyl with 1–4 C atoms, phenyl or benzyl, m is 2–20, o, p and q are positive integers each independently being less than or equal to 16, x and y are each independently 0, 1 or 2, Z$_1$ is a cis—CH=CH— group, a trans—CH=CH— group or a —C≡C— group, Z$_2$ is oxygen, sulfur, an NH-, an N-methyl or a —C≡C— group, and R$^{12}$ is a free or protected amino, hydroxy, carboxy, mercapto or halogen, comprising adding to a prochiral ketone of formula II

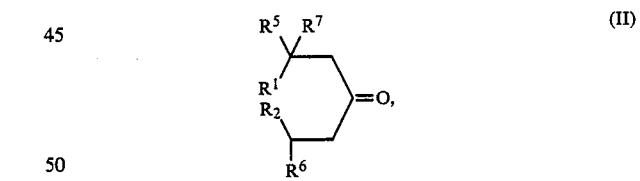

wherein R$^1$, R$^2$, R$^5$, R$^6$ and R$^7$ have the meanings indicated above, a lithiosulfoximine from a solution of n-butyllithium and an N-substituted S-methyl-S-phenyl-sulfoximine derivative of formula III

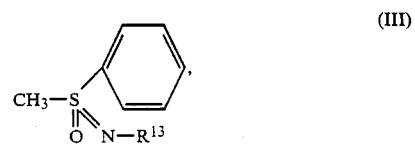

wherein R$^{13}$ has the meaning already indicated, and then reacting the thus formed product with n-butyllithium and trimethylchlorosilane.

2. A process of claim 1, wherein R$^1$ and R$^2$ are a common bond.

3. A process of claim 1, wherein $R^1$ and $R^2$ are the radical

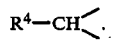

4. A process of claim 1, wherein $R^5$ and $R^6$ jointly are the radical

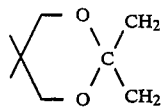

5. A process of claim 1, wherein $R^5$ and $R^6$ jointly are the radical

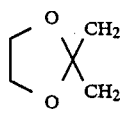

6. A process of claim 1, wherein $R^5$ and $R^6$ jointly are the radical

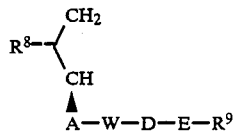

7. A process of claim 1, wherein $R^5$ and $R^6$ jointly are the radical

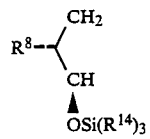

8. A process of claim 6, wherein $R^8$ is $OR^{10}$.
9. A process of claim 7, wherein $R^8$ is $OR^{10}$.
10. A process of claim 1, wherein $R^{13}$ is a tosyl radical.
11. A process of claim 1, wherein $R^{13}$ is a $C_4$ alkyl group.
12. A process of claim 3, wherein $R^4$ is t-butyl.
13. A process of claim 1, wherein $R^7$ is hydrogen.
14. A process of claim 1, wherein $R^7$ is the radical $-(CH_2)_m-R^{12}$.
15. A process of claim 1, wherein $R^7$ is the radical $-(CH_2)_{m-o}-[Z_1-(CH_2)_{m-p}]_x-[Z_2-(CH_2)_{m-q}]_y-R^{12}$.
16. A process of claim 8, wherein $R^{10}$ is a silyl radical.
17. A process of claim 9, wherein $R^{10}$ is a silyl radical.
18. A process of claim 8, wherein $R^{10}$ is an ether or an acid radical.
19. A process of claim 9, wherein $R^{10}$ is an ether or an acid radical.

* * * * *